(12) United States Patent
Thienphrapa et al.

(10) Patent No.: US 11,589,943 B2
(45) Date of Patent: Feb. 28, 2023

(54) TORSIONAL DEPLOYMENT DETECTION OF A VASCULAR THERAPY

(71) Applicant: KONINKLIJKE PHILIPS N.V., Eindhoven (NL)

(72) Inventors: Paul Thienphrapa, Cambridge, MA (US); Pascal Yves Francois Cathier, Asnières-sur-Seine (FR); Ashish Panse, Burlington, MA (US); Molly Lara Flexman, Melrose, MA (US); Torre Michelle Bydlon, Melrose, MA (US); Neriman Nicoletta Kahya, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 355 days.

(21) Appl. No.: 16/954,700

(22) PCT Filed: Dec. 19, 2018

(86) PCT No.: PCT/EP2018/085802
§ 371 (c)(1),
(2) Date: Jun. 17, 2020

(87) PCT Pub. No.: WO2019/121889
PCT Pub. Date: Jun. 27, 2019

(65) Prior Publication Data
US 2021/0085421 A1    Mar. 25, 2021

Related U.S. Application Data

(60) Provisional application No. 62/607,983, filed on Dec. 20, 2017.

(51) Int. Cl.
G06K 9/00    (2022.01)
A61F 2/07    (2013.01)
(Continued)

(52) U.S. Cl.
CPC ........ *A61B 90/06* (2016.02); *A61B 17/00234* (2013.01); *A61B 34/20* (2016.02);
(Continued)

(58) Field of Classification Search
CPC .................................. G06K 9/00; A61F 2/07
(Continued)

(56) References Cited

U.S. PATENT DOCUMENTS

| | | | | |
|---|---|---|---|---|
| 4,899,732 A | * | 2/1990 | Cohen | A61B 1/0052 600/161 |
| 6,808,534 B1 | * | 10/2004 | Escano | A61F 2/958 623/1.13 |

(Continued)

FOREIGN PATENT DOCUMENTS

| | | |
|---|---|---|
| WO | 2015071343 | 5/2015 |
| WO | 2016/116823 | 7/2016 |
| WO | 2016116821 | 7/2016 |

OTHER PUBLICATIONS

International Search Report and Written Opinion dated Mar. 19, 2019 for International Application No. PCT/EP2018/058502 filed Dec. 19, 2018.

(Continued)

*Primary Examiner* — Seyed H Azarian

(57) ABSTRACT

A torque detection vascular therapy system employing a vascular therapy device (101) and a torque detection controller (130). The vascular therapy device (101) is operable to be transitioned from a pre-deployed state to a post-deployed state, and includes a matrix of imageable markers representative of a geometry of the vascular therapy device (101). The torque detection controller (130) controls a detection of a non-torsional deployment or a torsional deployment of the vascular therapy device (101) subsequent to a transition of the vascular therapy device (101) from the pre-deployed state to the post-deployed state by deriving a (Continued)

vector indication of the non-torsional deployment or the torsional deployment of the vascular therapy device (101) from a matrix orientation similarity or a matrix orientation dissimilarity between a baseline device geometry of the vascular therapy device (101) represented by the matrix of the imageable markers and an imaged device geometry of the vascular therapy device (101) represented by the matrix of imageable markers.

20 Claims, 19 Drawing Sheets

(51) Int. Cl.
   *A61B 90/00* (2016.01)
   *A61B 34/20* (2016.01)
   *A61B 17/00* (2006.01)
   *A61F 2/962* (2013.01)

(52) U.S. Cl.
   CPC ...... *A61B 90/39* (2016.02); *A61B 2034/2061* (2016.02); *A61B 2034/2065* (2016.02); *A61B 2090/066* (2016.02); *A61B 2090/3966* (2016.02); *A61F 2/962* (2013.01)

(58) Field of Classification Search
   USPC ....... 382/100, 103, 107, 128–132, 168, 173, 382/181, 219, 224, 254, 276, 286, 312; 623/1.13, 1.36; 600/161; 606/7, 130
   See application file for complete search history.

(56) References Cited

U.S. PATENT DOCUMENTS

| 8,535,370 | B1* | 9/2013 | Eckert | A61F 2/07 |
| | | | | 623/1.13 |
| 2002/0091439 | A1* | 7/2002 | Baker | A61B 17/11 |
| | | | | 623/1.36 |
| 2013/0071001 | A1* | 3/2013 | Waechter-Stehle | G06T 7/73 |
| | | | | 382/132 |
| 2016/0310303 | A1* | 10/2016 | Thapliyal | A61F 2/856 |

OTHER PUBLICATIONS

Asrar ul Haq, et al: ", The invasive assessment of coronary atherosclerosis and stents using optical coherence tomography: a clinical update", Heart Asia 2013; 5: 154-161. doi: 10.1136/heartasia-2013-010328.

* cited by examiner

58a
Distal

Proximal

58b
Distal

Proximal

58c
Distal

Proximal

58d
Distal

Proximal

58e
Distal

R1:

R2:

R3:

Proximal

58f
Distal

R1:

R2:

R3:

R4:

R5:

R6:

R7:

Proximal

TORSIONAL DEPLOYMENT DETECTION OF A VASCULAR THERAPY

CROSS REFERENCE TO RELATED APPLICATIONS

This application is the U.S. National Phase application under 35 U.S.C. § 371 of International Application No. PCT/EP2018/085802 filed Dec. 19, 2018, published as WO 2019/121889 on Jun. 27, 2019, which claims the benefit of U.S. Provisional Patent Application No. 62/607,983 filed Dec. 20, 2017. These applications are hereby incorporated by reference herein.

FIELD OF THE INVENTION

The present disclosure generally relates to vascular therapy devices (e.g., endograft and stents). The present disclosure more particularly relates to a detection of a torsional deployment of a vascular therapy device during minimally invasive endovascular interventions (e.g., a torsional deployment of an endograft during an endovascular aneurysm repair ("EVAR") or a fenestrated EVAR ("FEVAR") repair of an abdominal aortic aneurysm ("AAA") or a torsional deployment of a stent during an angioplasty).

BACKGROUND OF THE INVENTION

As known in the art the present disclosure, an aorta is a main artery of a body that carries oxygen-rich blood from a heart through the body. An abdominal aorta aneurysm ("AAA") is a bulge/ballooning in a weakened section of the aorta within an abdominal region of the body whereby the aorta may rupture and cause excessive internal bleeding within the abdomen that quickly results in death.

For example, FIG. 1A illustrates an aorta 11 within an abdomen 10R,L including a right renal artery 12R, a left renal artery 12L, a right iliac artery 13R and a left iliac artery 13L branching from abdominal aorta 11. Shown within abdominal aorta 11 between artery branches 12 and 13 is an aneurysm 14R,L that may have been caused by various factors including high blood pressure, atherosclerosis and aging. Typical blood flow through aorta 11 to aortic branches 12 and 13 as symbolized by the dashed arrows strains the walls of aneurysm 14, which may cause aorta 11 to balloon, eventually leading to rupture, which can cause excessive internal bleeding within abdomen 10 that quickly results in death.

Various procedures have been proposed to repair AAA, of which, endovascular aneurysm repair ("EVAR") and fenestrated EVAR ("FEVAR") are currently the most common techniques for the repair of an AAA. An Endovascular procedure is typically carried out under x-ray fluoroscopy guidance and uses significant amounts of contrast and radiation to correctly position and orient an endovascular stent-graft ("endograft") within the abdominal aorta for deploying the endograft to control the flow of blood through the AAA.

For example, FIG. 1B illustrates an endograft 20 that was deployed under x-ray fluoroscopy guidance in abdominal aorta 11 to maintain continual blood flow to aortic branches 12 and 13 while reducing pressure along the walls of aneurysm 14.

By further example, FIG. 1C illustrates a fenestrated endograft 21 with branch grafts 22 that were deployed under x-ray fluoroscopy guidance in abdominal aorta 11 to maintain continual blood flow to aortic branches 12 and 13 while impeding blood flood away along the walls of aneurysm 14.

Also as known in the art of the present disclosure, an aorta branches off into two main coronary arteries, which a right coronary artery that supplying blood to a right side of a heart and a left coronary artery supplying blood to a left side of the heart. For various reasons, plaque may buildup in a coronary artery leading to a reduction of blood flow through the coronary artery. Such a reduction in blood flow will eventually result in chest pain and possibly a heart attack.

For example, FIG. 2A illustrates a buildup of plaque 31a and plaque 31b on the inner walls of a coronary artery 30 narrowing a passage 32 between plague 31a and plaque 31b that reduces blood flow through coronary artery 30.

A percutaneous coronary intervention ("PCI") or angioplasty involves an insertion of a balloon-tipped catheter into a coronary artery whereby the balloon is positioned in the opening and inflated to compress plaque to thereby open the passage. As the balloon is inflated, a collapsed stent over the balloon is expanded whereby the stent locks open passage to thereby improve blood flow, which relieves any chest pain and decreases the probability of a heart attack.

For example, FIG. 2B illustrates an expanded stent 40 locked into passage 32 to thereby improve blood flow through the compressed plague 31a and 31b, which relieves any chest pain and decreases a probability of a heart attack.

As shown in FIGS. 1A, 1C and 2B, vascular therapy devices are regarded as elongated devices that conform to the walls of blood vessels while allowing blood to flow through by augmenting the structure of diseased vessel walls. Such vascular therapy devices are thus made to be firm in the radial direction to enforce wall structure, while flexible in the axial ("long") direction to conform to tortuous blood vessels.

A negative side effect of this property of vascular therapy devices is that these devices may torque axially during delivery and become deployed in the patient in a twisted configuration (i.e., a torsional deployment). This condition may exert undesired forces on the tissue of the blood vessel, facilitate an unstable build-up of energy that when released can cause damage to the surrounding tissue of the blood vessel, and furthermore compromise the placement and thus effectiveness of the device.

SUMMARY OF THE INVENTION

Endovascular surgery as known in the art generally is a minimally invasive intervention involving access through major blood vessels to a targeted area of a cardiovascular system including a heart and all blood vessels. Examples of endovascular surgery include, but are not limited to, EVAR, FEVAR, coronary stenting, peripheral vascular ballooning and stenting, mitral valve replacement, mitral clip placement, aortic valve replacement, left atrial appendage closure, perivalvular leak closure, etc.

The present disclosure proposes a novel and unique autonomous detection of a non-torsional deployment or a torsional deployment of a vascular therapy device during endovascular surgery and alerting clinicians of any detection of the torsional deployment of the vascular therapy device during the endovascular surgery.

One embodiment of the present disclosure is a torque detection vascular therapy system employing a vascular therapy device (e.g., an endograft or a stent) and a torque detection controller. The vascular therapy device is operable to be transitioned from a pre-deployed state to a post-deployed state, and includes a matrix of imageable markers representative of a geometry of the vascular therapy device. The torque detection controller controls a detection of either a non-torsional deployment or a torsional deployment of the vascular therapy device subsequent to a transition of the vascular therapy device from the pre-deployed state to the post-deployed state. A detection by the torque detection controller of the non-torsional deployment is derived from a matrix orientation similarity between a baseline device geometry of the vascular therapy device represented by the matrix of the imageable markers and an imaged device geometry of the vascular therapy device represented by the matrix of imageable markers. A detection by the torque detection controller of the torsional deployment is derived from a matrix orientation dissimilarity between the baseline device geometry of the vascular therapy device represented by the matrix of the imageable markers and the imaged device geometry of the vascular therapy device represented by the matrix of imageable markers.

A second embodiment of the present disclosure is the torque detection employing a geometry manager and a torque detector. In operation, the geometry manager manages a delineation of the baseline device geometry of the vascular therapy device represented by the matrix of the imageable markers and a delineation of the imaged device geometry of the vascular therapy device represented by the matrix of imageable markers. A detection by the torque detector of the non-torsional deployment is derived from a matrix orientation similarity between a baseline device geometry of the vascular therapy device represented by the matrix of the imageable markers and an imaged device geometry of the vascular therapy device represented by the matrix of imageable markers. A detection by the torque detector of the torsional deployment is derived from a matrix orientation dissimilarity between the baseline device geometry of the vascular therapy device represented by the matrix of the imageable markers and the imaged device geometry of the vascular therapy device represented by the matrix of imageable markers.

A third embodiment of the present disclosure is a torque detection method executed by the torque detection controller. The torque detection method involves the torque detection controller managing the delineation of the baseline device geometry of the vascular therapy device represented by the matrix of the imageable markers and the delineation of the imaged device geometry of the vascular therapy device represented by the matrix of imageable markers. The torque detection vascular therapy method further involves the torque detection controller deriving a detection of the non-torsional deployment of the vascular therapy device from the matrix orientation similarity between the baseline device geometry of the vascular therapy device represented by the matrix of the imageable markers and the imaged device geometry of the vascular therapy device represented by the matrix of imageable markers, or deriving a detection of the torsional deployment of the vascular therapy device from a matrix orientation dissimilarity between the baseline device geometry of the vascular therapy device represented by the matrix of the imageable markers and the imaged device geometry of the vascular therapy device represented by the matrix of imageable markers.

For purposes of describing and claiming the inventions of the present disclosure:

(1) the term "vascular therapy device" broadly encompasses all devices, as known in the art of the present disclosure and hereinafter conceived, for applying a therapy to a vascular anatomy to control blood flow through the vascular anatomy. Examples of a vascular therapy device includes an endograft and a stent;

(2) the term "imageable marker" broadly encompasses any feature/component of a vascular therapy device discernable within an extravascular imaging or an intravascular imaging of the vascular therapy device. Examples of an imageable marker include, but are not limited to, a radiopaque feature/component of a vascular therapy device, an ultrasound sensitive feature/component of a vascular therapy device, and an optical sensitive feature/component of a vascular therapy device;

(3) the term "matrix of imageable markers" broadly encompasses two or more imageable markers arranged relative to a longitudinal axis of a vascular therapy device. Examples of a matrix of imageable markers include an arrangement of segregated imageable markers partially or fully encircling a vascular therapy device, torque sensor embodying an arrangement of segregated imageable markers, an arrangement of segregated torque sensors partially or fully encircling a vascular therapy device;

(4) the term "non-torsional deployment" broadly encompasses a deployment of a vascular therapy device excluding any detectable torque being applied to the vascular therapy device via an extravascular imaging or an intravascular imaging of the vascular therapy device;

(5) the term "torsional deployment" broadly encompasses a deployment of a vascular therapy device including a detectable torque being applied to the vascular therapy device via an extravascular imaging or an intravascular imaging of the vascular therapy device;

(6) the term "matrix orientation similarity" broadly encompasses a system-defined similarity between an orientation of the matrix of imageable markers at a pre-deployed state of the vascular therapy device relative to a longitudinal axis of the vascular therapy device and an orientation of the matrix of imageable markers at a post-deployed state of the vascular therapy device relative to the longitudinal axis of the vascular therapy device;

(7) the term "matrix orientation dissimilarity" broadly encompasses a system-defined dissimilarity between the orientation of the matrix of imageable markers at a pre-deployed state of the vascular therapy device relative to a longitudinal axis of the vascular therapy device and the orientation of the matrix of imageable markers at a post-deployed state of the vascular therapy device relative to the longitudinal axis of the vascular therapy device;

(8) the term "vascular therapy method" broadly encompasses all procedures, as known in the art of the present disclosure and hereinafter conceived, for implementing an endovascular surgery. Examples of a vascular therapy method include, but are not limited to, an endovascular aneurysm repair of an abdominal aortic aneurysm, a fenestrated endovascular aneurysm repair of an abdominal aortic aneurysm, angioplasty, coronary stenting, peripheral vascular ballooning and stenting, mitral valve replacement, mitral clip placement, aortic valve replacement, left atrial appendage closure and perivalvular leak closure;

(9) the term "vascular therapy system" broadly encompasses all medical systems, as known in the art of the present disclosure and hereinafter conceived, for executing a vascular therapy method. Examples of such medical systems include, but are not limited to, a endograft systems for delivery of the vascular therapy device (e.g., Medtronic Endurant II™, Cook Zenith Flex®, Endologix AFX®2 and Gore® Excluder®) and an imaging system for imaging the delivery of the vascular therapy device (e.g., Philips Azurion™ and Siemens Artis™);

(10) the term "torque detection vascular therapy method" broadly encompasses all vascular therapy methods incorporating the inventive principles of the present disclosure for a detection of a non-torsional deployment or a torsional deployment of a vascular therapy device during an endovascular surgery;

(11) the term "torque detection vascular therapy system" broadly encompasses all vascular therapy system incorporating the inventive principles of the present disclosure for a detection of a non-torsional deployment or a torsional deployment of a vascular therapy device during an endovascular surgery;

(12) the term "controller" broadly encompasses all structural configurations, as understood in the art of the present disclosure and as exemplary described in the present disclosure, of an application specific main board or an application specific integrated circuit for controlling an application of various inventive principles of the present disclosure as exemplary described in the present disclosure. The structural configuration of the controller may include, but is not limited to, processor(s), computer-usable/computer readable storage medium(s), an operating system, application module (s), peripheral device controller(s), slot(s) and port(s). A controller may be housed within or linked to an augmented reality device, a medical device and/or a workstation. Examples of a "workstation" include, but are not limited to, an assembly of one or more computing devices, a display/monitor, and one or more input devices (e.g., a keyboard, joysticks and mouse) in the form of a standalone computing system, a client computer of a server system, a desktop, a laptop or a tablet;

(13) the descriptive labels for controllers described and claimed herein facilitate a distinction between controllers as described and claimed herein without specifying or implying any additional limitation to the term "controller";

(14) the term "application module" broadly encompasses an application incorporated within or accessible by a controller consisting of an electronic circuit (e.g., electronic components and/or hardware) and/or an executable program (e.g., executable software stored on non-transitory computer readable medium(s) and/or firmware) for executing a specific application;

(15) the descriptive labels for application modules described and claimed herein facilitate a distinction between application modules as described and claimed herein without specifying or implying any additional limitation to the term "controller";

(16) the terms "signal", "data" and "command" broadly encompasses all forms of a detectable physical quantity or impulse (e.g., voltage, current, or magnetic field strength) as understood in the art of the present disclosure and as exemplary described in the present disclosure for transmitting information and/or instructions in support of applying various inventive principles of the present disclosure as subsequently described in the present disclosure. Signal/data/command communication various components of the present disclosure may involve any communication method as known in the art of the present disclosure including, but not limited to, signal/data/command transmission/reception over any type of wired or wireless datalink and a reading of signal/data/commands uploaded to a computer-usable/computer readable storage medium; and

(17) the descriptive labels for signals/data/commands as described and claimed herein facilitate a distinction between signals/data/commands as described and claimed herein without specifying or implying any additional limitation to the terms "signal", "data" and "command".

The foregoing embodiments and other embodiments of the inventions of the present disclosure as well as various features and advantages of the inventions of the present disclosure will become further apparent from the following detailed description of various embodiments of the inventions of the present disclosure read in conjunction with the accompanying drawings. The detailed description and drawings are merely illustrative of the inventions of the present disclosure rather than limiting, the scope of the inventions of the present disclosure being defined by the appended claims and equivalents thereof.

DETAILED DESCRIPTION OF THE PREFERRED EMBODIMENTS

Figure 1A:
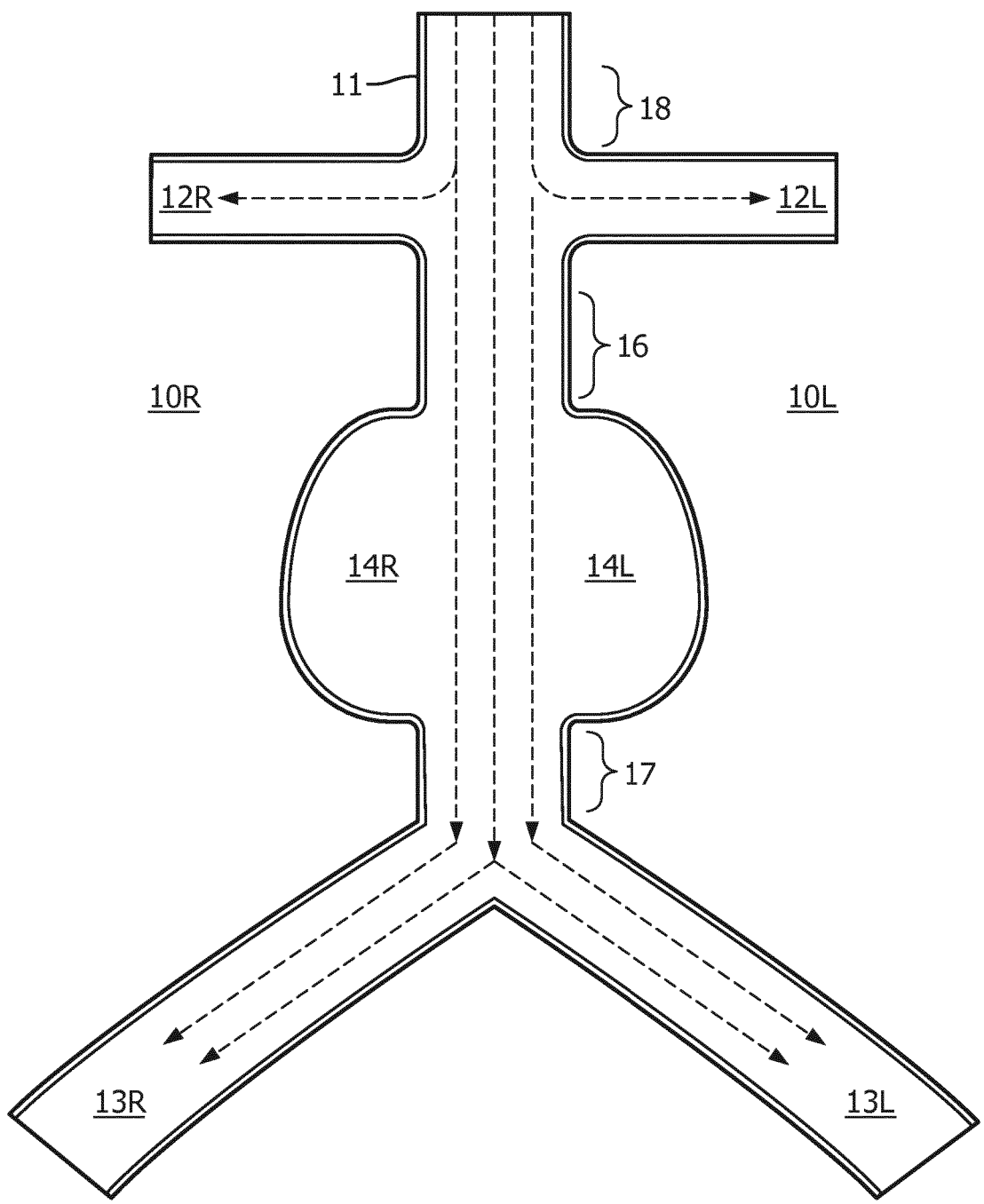
FIGS. 1A-1C illustrate an exemplary endograft deployment for repairing an abdominal aorta aneurysm as known in the art.
Figure 1B:
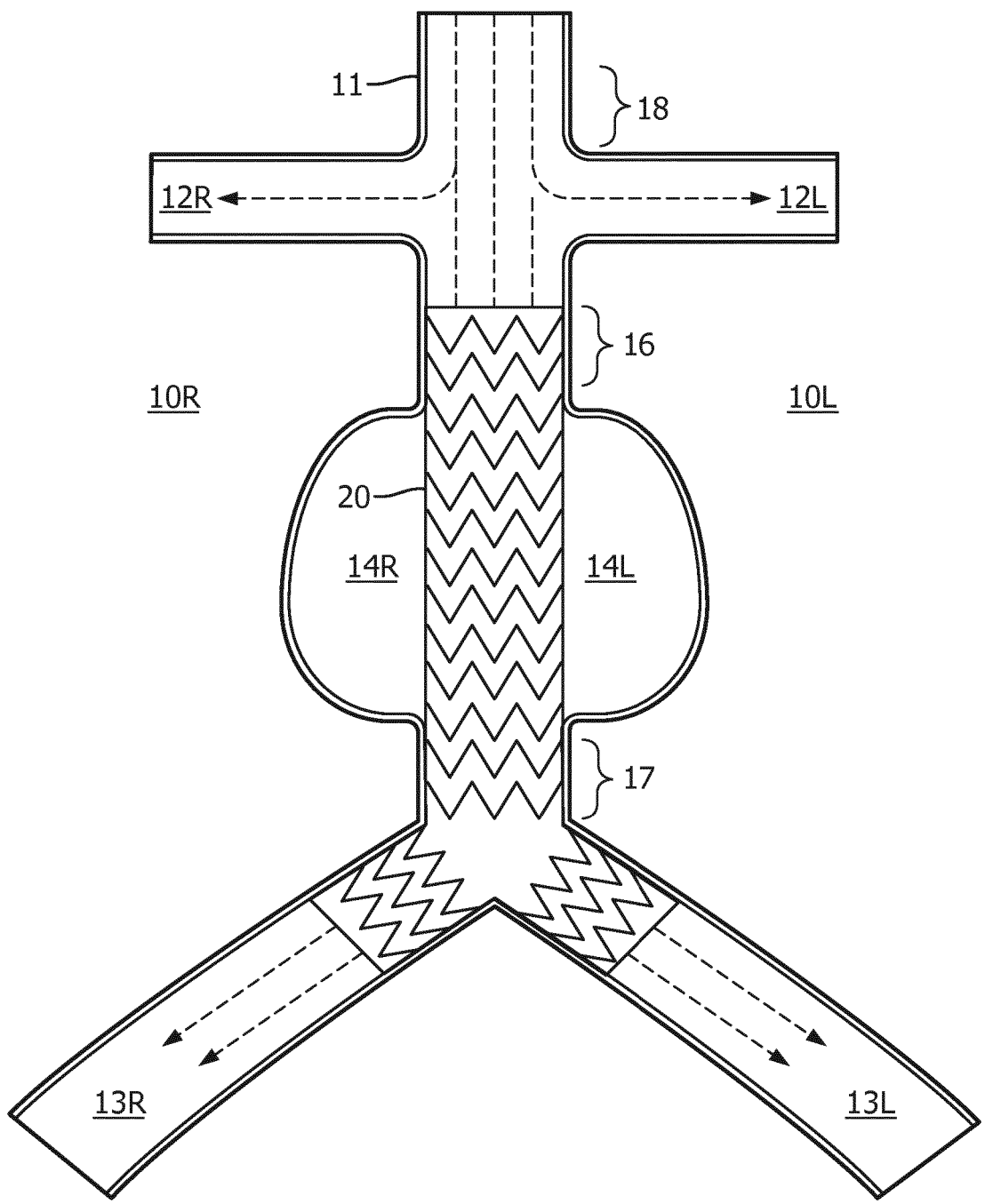
Figure 1C:
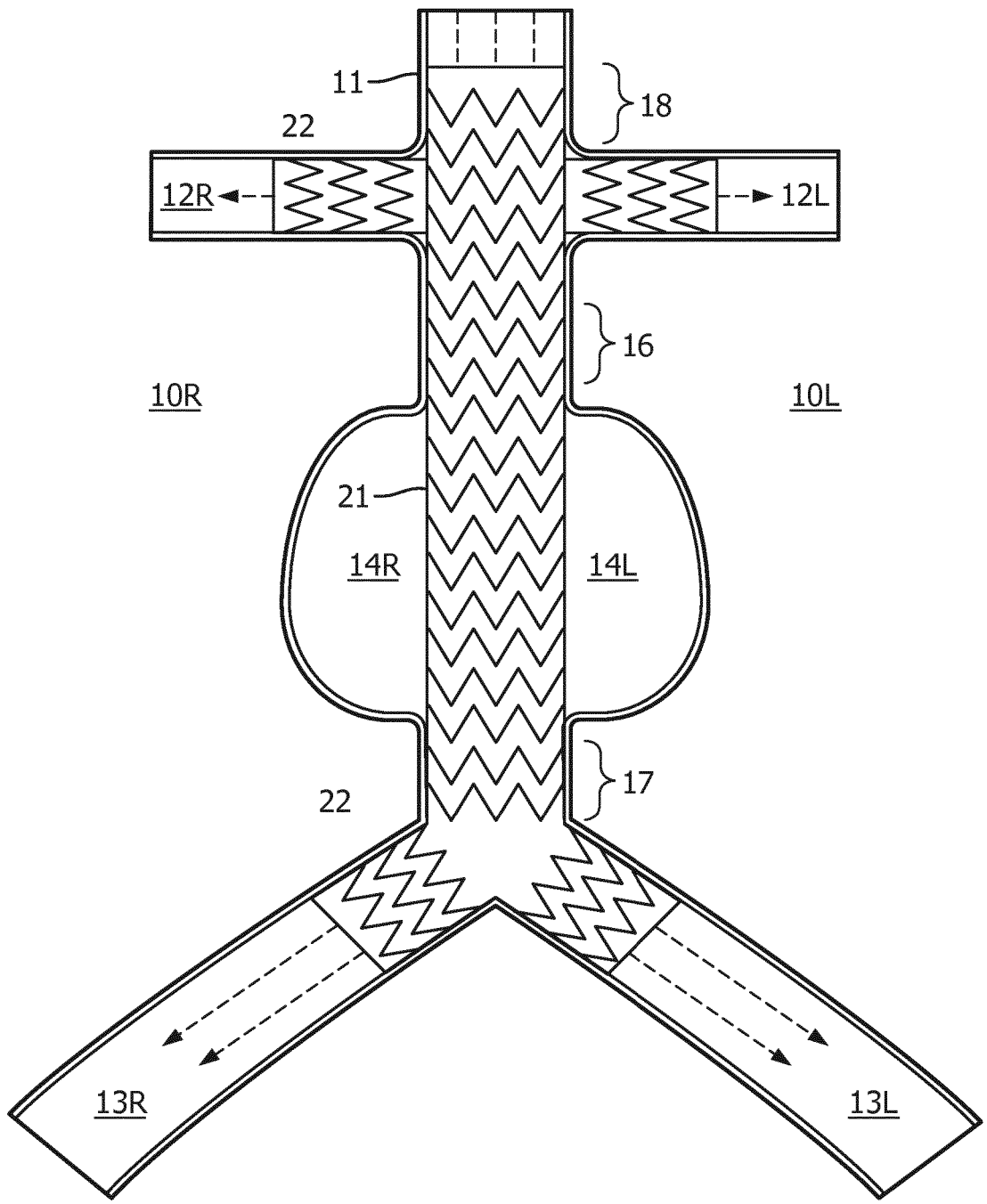
Figure 2A:
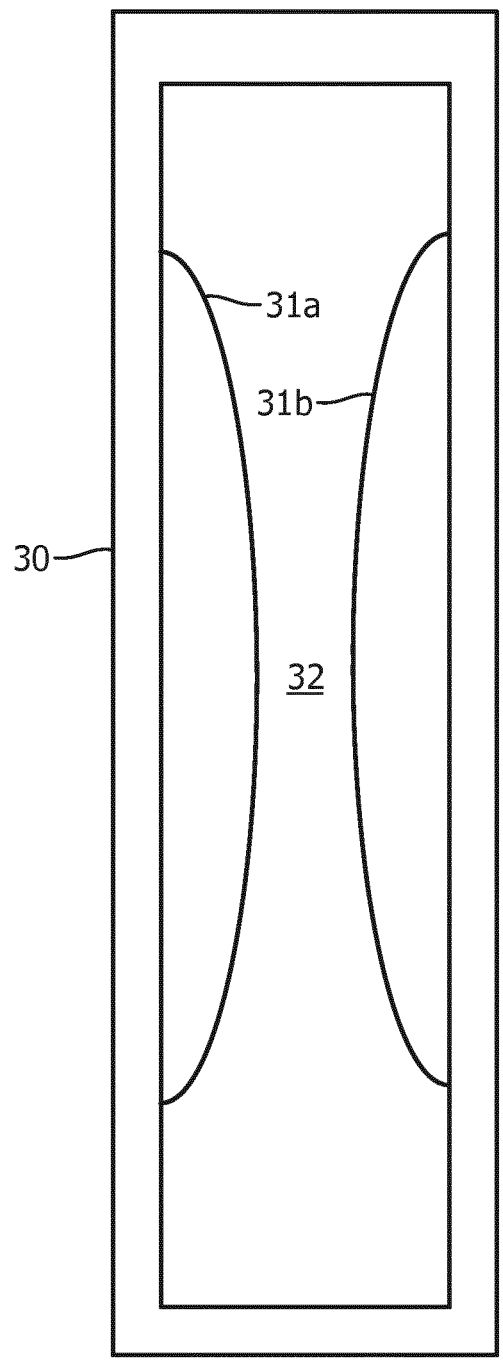
FIGS. 2A and 2B illustrate an exemplary stent deployment for compressing plague buildup as known in the art.
Figure 2B:
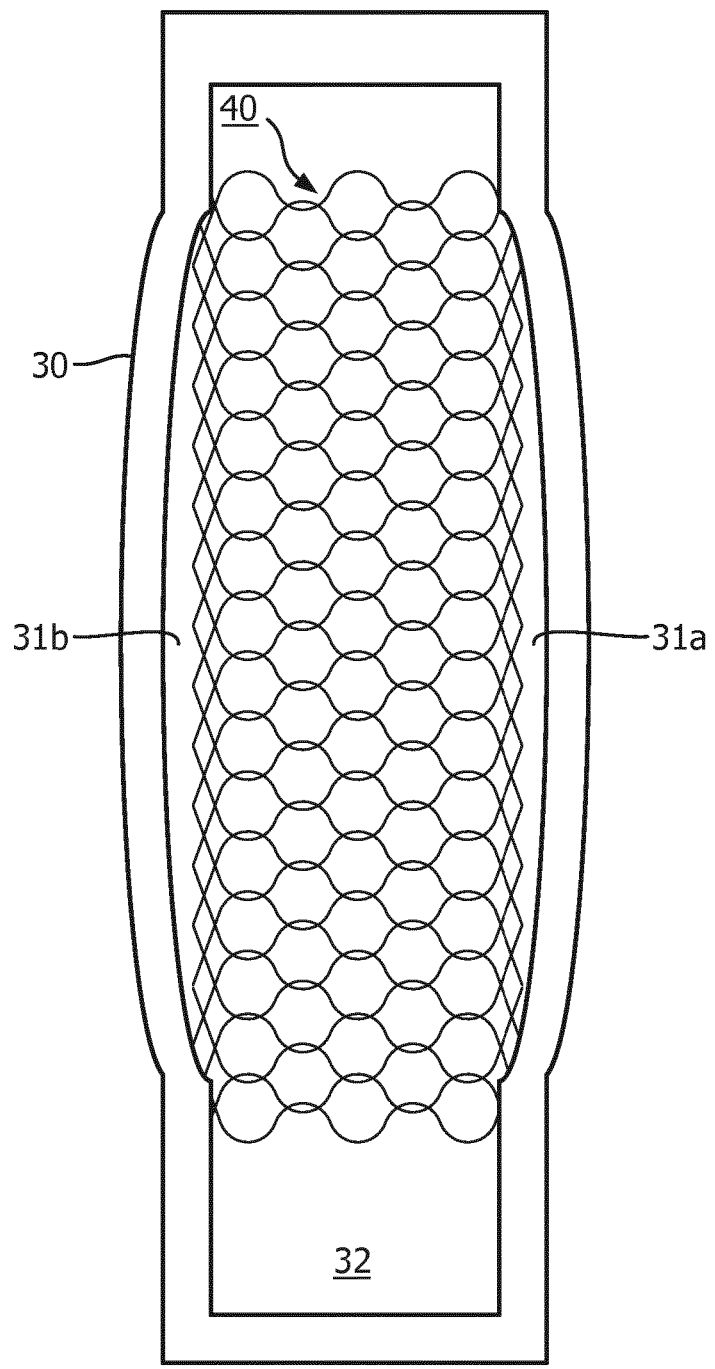

The inventions of the present disclosure involve a detection of a non-torsional deployment or a torsional deployment of a vascular therapy device (e.g., an endograft, a stent, etc.) subsequent to a transition of the vascular therapy device from a pre-deployed state to a post-deployed state. In practice of the present disclosure, a deployed state of a vascular therapy device is any physical state of the vascular therapy device ranging between an undeployed compressed physical state of the vascular therapy device for navigating the vascular therapy device within a vascular anatomy and a fully deployed expanded physical state of the vascular therapy device for permanently positioning the vascular therapy device within the vascular anatomy.

For example, an undeployed compressed physical state of an endograft for navigating the vascular therapy device within a vascular anatomy involves the endograft being compressed within a catheter sheath as known in the art of the present disclosure, and a fully deployed expanded physical state of the endograft involves an unsheathing of the endograft to thereby expand the endograft for permanently positioning the endograft within the vascular anatomy as known in the art of the present disclosure.

By further example, an undeployed compressed physical state of a stent for navigating the vascular therapy device within a vascular anatomy involves the stent being compressed with a deflated balloon positioned within the stent as known in the art of the present disclosure, and a fully deployed expanded physical state of the endograft involves an inflating of the balloon catheter to thereby expand the stent for permanently positioning the stent within the vascular anatomy as known in the art of the present disclosure.

For purposes of a detecting a non-torsional deployment or a torsional deployment of the vascular therapy device in accordance with the present disclosure subsequent to a transition of the vascular therapy device from a pre-deployed state to a post-deployed state, the pre-deployed state of the vascular therapy device may be any physical state of the vascular therapy device excluding a fully deployed expansion physical state of the vascular therapy device, and a post-deployed state of the vascular therapy device may be any physical state of the vascular therapy device excluding an undeployed compressed physical state of the vascular therapy device. More particularly, the pre-deployed state of the vascular therapy device ranges between a compressed physical state and any partially expanded physical state of the vascular therapy device, and the post-deployed state of the vascular therapy device ranges between any partially expanded physical state and a fully expanded physical state of the vascular therapy device.

In practice of the present disclosure, one or more detections of a non-torsional deployment or a torsional deployment of the vascular therapy device in accordance with the present disclosure may be executed subsequent to a transition of the vascular therapy device from a pre-deployed state to a post-deployed state.

In one embodiment, more particularly for an endovascular surgery involving a minimal degree of imaging of a vascular anatomy, a single detection of a non-torsional deployment or a torsional deployment of the vascular therapy device in accordance with the present disclosure may be executed subsequent to a transition of the vascular therapy device from an undeployed compressed physical state (the pre-deployed state) to a fully deployed expanded physical state (the post-deployed state).

In a second embodiment, more particularly for an endovascular surgery involving a minimal degree of imaging of a vascular anatomy, a single detection of a non-torsional deployment or a torsional deployment of the vascular therapy device in accordance with the present disclosure may be executed subsequent to a transition of the vascular therapy device from an undeployed compressed physical state (the pre-deployed state) to a partially deployed expanded physical state (the post-deployed state).

In a third embodiment, more particularly for an endovascular surgery involving a minimal degree of imaging of a vascular anatomy, a single detection of a non-torsional deployment or a torsional deployment of the vascular therapy device in accordance with the present disclosure may be executed subsequent to a transition of the vascular therapy device from a partially deployed expanded physical state (the pre-deployed state) to a fully deployed expanded physical state (the post-deployed state).

In a fourth embodiment, more particularly for an endovascular surgery involving an intermittent imaging of a vascular anatomy, intermittent detections of a non-torsional deployment or a torsional deployment of the vascular therapy device in accordance with the present disclosure may be executed as the vascular therapy device is transitioned from an undeployed compressed physical state (the pre-deployed state) to a deployed expanded physical state (the post-deployed state). For example, an initial detection of a non-torsional deployment or a torsional deployment of the vascular therapy device in accordance with the present disclosure may be executed as the vascular therapy device is transitioned from an undeployed compressed physical state (an initial pre-deployed state) to a partially deployed expanded physical state (an initial post-deployed state), and a final detection of a non-torsional deployment or a torsional deployment of the vascular therapy device in accordance with the present disclosure may be executed as the vascular therapy device is transitioned from the partially deployed expanded physical state (a final pre-deployed state) to a fully deployed expanded physical state (a final post-deployed state).

In a fifth embodiment, more particularly for an endovascular surgery involving a periodic imaging or a continual imaging of a vascular anatomy, periodic detections of a non-torsional deployment or a torsional deployment of the vascular therapy device in accordance with the present disclosure may be executed as the vascular therapy device is transitioned from an undeployed compressed physical state (the pre-deployed state) to a deployed expanded physical state (the post-deployed state). For example, an initial detection of a non-torsional deployment or a torsional deployment of the vascular therapy device in accordance with the present disclosure may be executed as the vascular therapy device is transitioned from an undeployed compressed physical state (an initial pre-deployed state) to a partially deployed expanded physical state (an initial post-deployed state), periodic detections of a non-torsional deployment or a torsional deployment of the vascular therapy device in accordance with the present disclosure may be executed as the vascular therapy device is further expanded, and a final detection of a non-torsional deployment or a torsional deployment of the vascular therapy device in accordance with the present disclosure may be executed as the vascular therapy device is transitioned from a partially deployed expanded physical state (a final pre-deployed state) to a fully deployed expanded physical state (a final post-deployed state).

To facilitate a further understanding of the present disclosure, exemplary embodiments of a vascular therapy device of the present disclosure will now be described in connection with FIGS. 3A and 3B. From the description of FIGS. 3A and 3B, those having ordinary skill in the art will understand how to make and use additional varied and numerous embodiments of a vascular therapy device in accordance with the present disclosure.

Figure 3A:
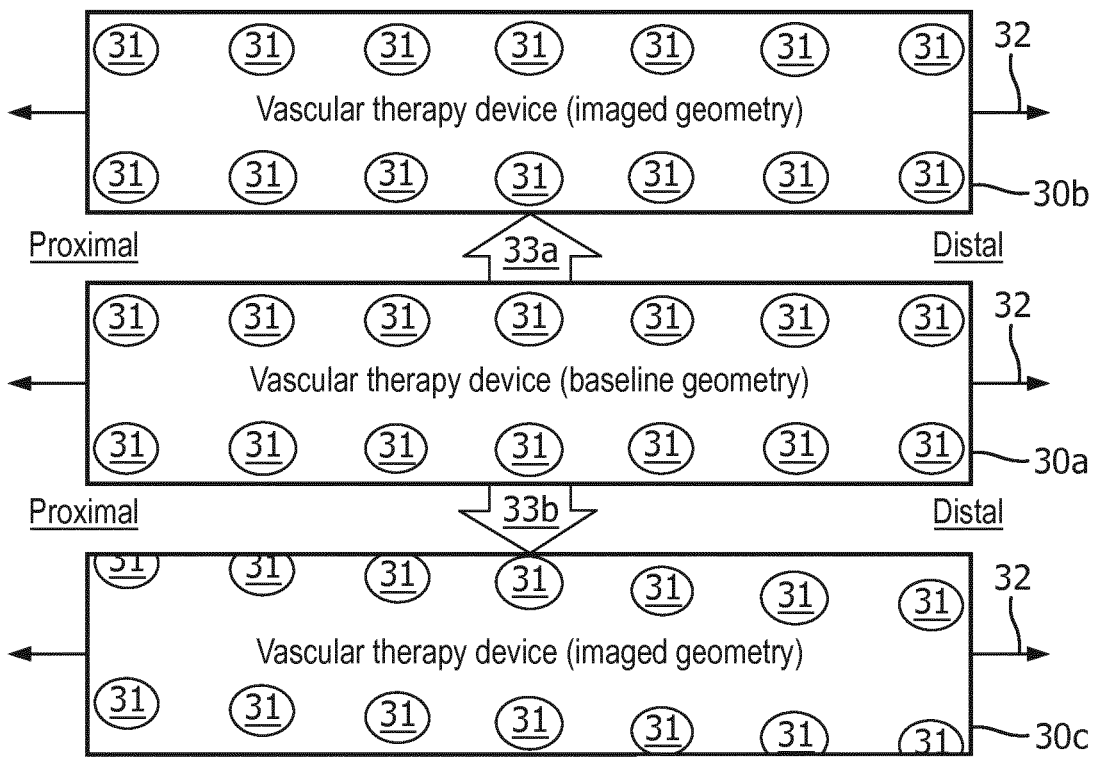
FIG. 3A illustrates an exemplary embodiment of a vascular therapy device in accordance with the inventive principles of the present disclosure.
Figure 3B:
FIG. 3B illustrates an exemplary embodiment of a torque sensor in accordance with the inventive principles of the present disclosure.

Referring to FIG. 3A, a vascular therapy device 30a-c of the present disclosure employs a matrix of two or more imageable markers 31 oriented relative to a longitudinal axis 32 of device 30 (fourteen (14) imageable markers 31 are exemplary shown), whereby the matrix of imageable markers 31 represents a geometry of vascular therapy device 30. As will be further described in the present disclosure, the orientation of the matrix of imageable markers 31 relative to longitudinal axis 32 facilitates a detection of an exemplary non-torsional deployment 33a of vascular therapy device 30 based on a matrix orientation similarity between a baseline device geometry 30a of vascular therapy device 30 represented by the matrix of imageable markers 31 and an imaged device geometry 30b of vascular therapy device 30 represented by the matrix of imageable markers 31. Additionally, the orientation of the matrix of imageable markers 31 relative to longitudinal axis 32 facilitates a detection of an exemplary torsional deployment 33b of vascular therapy device 30 based on a matrix orientation dissimilarity between baseline device geometry 30a of vascular therapy device 30 represented by the matrix of imageable markers 31 and an imaged device geometry 30c of vascular therapy device 30 represented by the matrix of imageable markers 31.

In practice of the present disclosure, vascular therapy device 30 may be any type of device utilized for an endovascular surgery, and imageable markers 31 may be any device feature of vascular therapy device 30 that is identifiable in an extravascular imaging and/or an intravascular imaging of vascular therapy device 30.

In one exemplary embodiment, vascular therapy device 30 is an endograft as known in the art of the present disclosure and imageable markers 31 are radiopaque markers as known in the art of the present disclosure. For this embodiment, the endograft has tubular metal webs adjoined to a woven polyester tube whereby each radiopaque marker is adjoined to one of the tubular metal webs to form a matrix of radiopaque markers having a baseline orientation relative to a longitudinal axis of the woven polyester tube.

In a second exemplary embodiment, vascular therapy device 30 is a stent as known in the art of the present disclosure and imageable markers 31 are ultrasound sensitive markers as known in the art of the present disclosure. For this embodiment, the stent is configured as a wire mesh tube whereby each ultrasound sensitive marker is adjoined to the wire mesh tube to form a matrix of ultrasound sensitive markers having a baseline orientation relative to a longitudinal axis of wire mesh tube.

Also in practice of the present disclosure, a configuration of the matrix of imageable markers 31 defines a pattern of points radially extending from longitudinal axis 32 and longitudinally extending along any portion or an entirety of vascular therapy device 30 from a proximal end of vascular therapy device 30 to a distal end of vascular therapy device 30.

In one exemplary embodiment, a configuration of the matrix of imageable markers 31 defines columns of points radially extending from longitudinal axis 32 with each column having equal spaced imageable markers 31 longitudinally extending over a portion or an entirety of vascular therapy device 30 between the proximal end of vascular therapy device 30 and the distal end of vascular therapy device 30. For example, as will be further described in the present disclosure, four columns of points may be radially spaced ninety degree (90°) with each column having equal spaced imageable markers 31 longitudinally extending from the proximal end of vascular therapy device 30 to the distal end of vascular therapy device 30.

In a second exemplary embodiment, a configuration of the matrix of imageable markers 31 defines rows of points radially extending from longitudinal axis 32 with each row having equal spaced imageable markers 31 encircling the vascular therapy device 30 and with each row of points being longitudinally misaligned from adjacent row(s) over a portion or an entirety of vascular therapy device 30 between the proximal end of vascular therapy device 30 and the distal end of vascular therapy device 30. For example, as will be further described in the present disclosure, multiple rows of points may be radially misaligned from adjacent row(s) along the vascular therapy device 30 and longitudinally extending from the proximal end of vascular therapy device 30 to the distal end of vascular therapy device 30.

Those having ordinary skill in the art of the present disclosure will appreciate a high accuracy in a detection of a non-torsional deployment (e.g., non-torsional deployment 33a) or a torsional deployment (e.g., torsional deployment 33b) of the vascular therapy device 30 with a dense matrix of imageable markers 31 extending between the proximal end of vascular therapy device 30 and the distal end of vascular therapy device 30.

Further in practice, the matrix of imageable markers 31 may be embodied in a torque sensor of the present disclosure. In one embodiment, a torque sensor 34 may be a host body having the matrix imageable markers 31 affixed therein as exemplary shown in FIG. 3B, whereby torque sensor 34 may be adjoined to tubular metal webs of an endograft or may be adjoined to a wire mesh tube of a stent. In a second embodiment, a torque sensor of the present disclosure may be a unitary imageable body having each imageable marker 31 designated as a point on the torque sensor, whereby the torque sensor may be adjoined to tubular metal webs of an endograft or may be adjoined to a wire mesh tube of a stent.

To facilitate a further understanding of the present disclosure, exemplary embodiments of a torque detection vascular therapy method of the present disclosure will now be described in connection with FIGS. 4-8B. From the description of FIGS. 4-8B, those having ordinary skill in the art will understand how to make and use additional varied and numerous embodiments of a torque detection vascular therapy method in accordance with the present disclosure.

Figure 4:
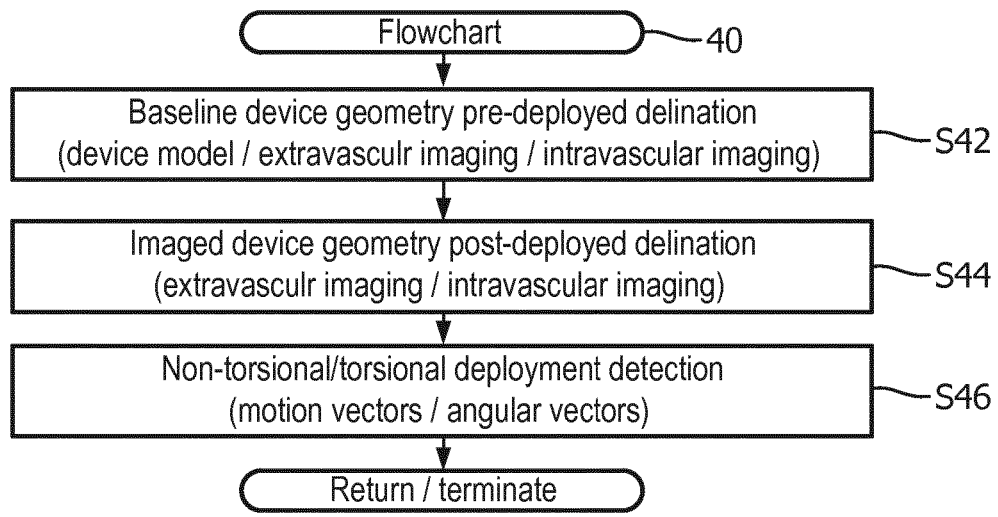
FIG. 4 illustrates a flowchart representative of an exemplary embodiment of a torque detection vascular therapy method in accordance with the inventive principles of the present disclosure.

Referring to FIG. 4, a flowchart 40 represents a torque detection vascular therapy method of the present disclosure involving a transition of a vascular therapy device of the present disclosure from a pre-deployed state to a post-deployed state.

A stage S42 of flowchart 40 encompasses a delineation of a baseline device geometry of the vascular therapy device associated with a pre-deployed state of the vascular therapy device.

In one exemplary embodiment of stage S42, a physical model or a digitized model of the vascular therapy device in any pre-deployed state may serve as a basis for a digital construction of a geometrical model of the matrix of imageable markers representing a baseline device geometry of the vascular therapy device. Techniques for such digital construction are known in the art of the present disclosure, such as, for example, digital models may be constructed prospectively using device design specifications.

In a second exemplary embodiment of stage S42, an extravascular imaging of a portion or an entirety of the vascular therapy device in any pre-deployed state within a vascular anatomy (e.g., X-ray imaging) may serve as a basis for a digital construction of a geometrical model of the imaged matrix of imageable markers representing a baseline device geometry of the vascular therapy device. Techniques for such digital construction are known in the art of the present disclosure, such as, for example, digital models may be constructed retrospectively by segmenting markers from a cone beam CT scan of a partially deployed device in the body.

In a third exemplary embodiment of stage S42, an intravascular imaging of a portion or an entirety of the vascular therapy device in any pre-deployed state within a vascular anatomy (e.g., ultrasound catheter imaging) may serve as a basis for a digital construction of a geometrical model of the image matrix of imageable markers representing a baseline device geometry of the vascular therapy device. Techniques for such digital construction are known in the art of the present disclosure, such as, for example, an intravascular ultrasound (IVUS) pullback technique involving a sequence of ultrasound images capturing vessel cross sections is acquired as the intravascular imaging device is pulled through the vessel segment of interest, the image sequence is fused to construct a 3D volumetric image containing the vascular therapy device, and markers from the device are segmented from the volume to form a digital model. Similarly, an optical coherence tomography (OCT) pullback technique may be utilized.

In a fourth exemplary embodiment of stage S42, a physical model or a digitized model of the vascular therapy device in an undeployed state may serve as a basis for a digital construction of a geometrical model of the matrix of imageable markers representing a baseline device geometry of the vascular therapy device, and an extravascular imaging or an intravascular image of a portion or an entirety of the vascular therapy device in any partially deployed state within a vascular anatomy (e.g., ultrasound catheter imaging) may serve as a basis for a dynamic update of the digital construction of the baseline geometrical model of the image matrix of imageable markers.

A stage S44 of flowchart 40 encompasses a delineation of an imaged device geometry of the vascular therapy device associated with a post-deployed state of the vascular therapy device. In one exemplary embodiment of stage S44, an extravascular imaging of the vascular therapy device in any post-deployed state within a vascular anatomy (e.g., X-ray imaging) may serve as a basis for a digital construction of a geometrical model of the matrix of imageable markers representing an imaged device geometry of the vascular therapy device. Techniques for such digital construction are known in the art of the present disclosure.

In a second exemplary embodiment of stage S44, an intravascular imaging of the vascular therapy device in any post-deployed state within a vascular anatomy (e.g., ultrasound catheter imaging) may serve as a basis for a digital construction of a geometrical model of the matrix of imageable markers representing an imaged device geometry of the vascular therapy device. Techniques for such digital construction are known in the art of the present disclosure, such as, for example, an IVUS pullback and an OCT pullback as previously described in the present disclosure.

A stage S46 of the flowchart 40 encompasses a detection of a non-torsional deployment or a torsional deployment of the vascular therapy device at the post-deployed state derived from a matrix orientation similarity or dissimilarity between the baseline device geometry of the vascular therapy device of stage S42 and the imaged device geometry of the vascular therapy device of stage S44. More particularly, the baseline geometrical model of the vascular therapy device represented by the matrix of the imageable markers of stage S42 and the measured geometrical model of the vascular therapy device represented by the matrix of the imageable markers of stage S44 are registered to an imaging space utilized during stage S44 whereby an orientation of the baseline geometrical model relative to the longitudinal axis of the vascular therapy device may be compared to an orientation of the imaged geometrical model relative to the longitudinal axis of the vascular therapy device to thereby detect a non-torsional deployment or a torsional deployment of the vascular therapy device at the post-deployed state.

In practice of the present disclosure, stage S46 may implement any technique suitable for comparing the orientations of the baseline geometrical model and the imaged geometrical model relative to the longitudinal axis of the vascular therapy device.

In one embodiment of stage S46, motion vectors between registered pairs of imageable markers between the baseline geometrical model and the imaged geometrical model are computed to provide an indication of a non-torsional deployment or a torsional deployment of the vascular therapy device to the post-deployed state.

S46: Exemplary Detection of a Non-Torsional Deployment of an Endograft.

Figure 5A:
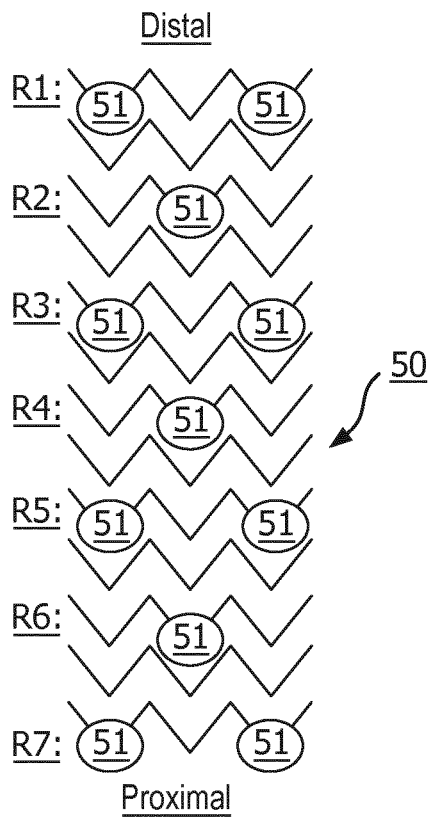
FIGS. 5A-5D illustrate a non-torsional deployment of an endograft as represented by the matrix of geometrical model of the endograft in accordance with the inventive principles of the present disclosure.
Figure 5B:
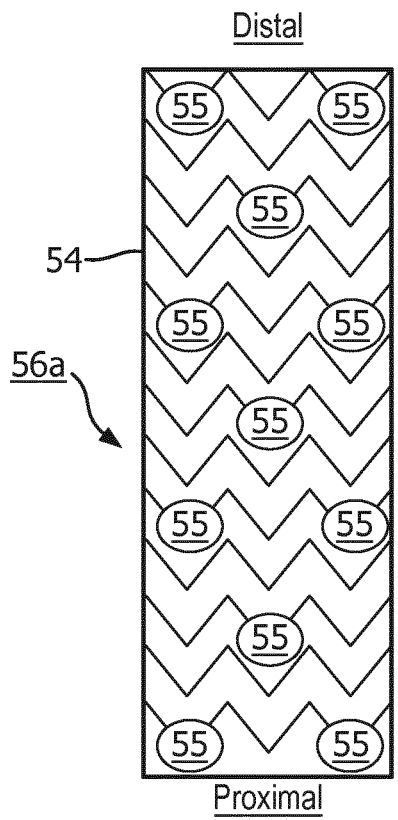

FIG. 5A illustrates a baseline geometrical model 50 digitally constructed from a device model, an extravascular imaging or an intravascular imaging of a fully expanded state 56a of an endograft 54 as shown in FIG. 5B. More particularly, endograft 54 consists of seven rows R1-R7 of imageable markers 55 extending between a proximal end and a distal end of endograft 54, and baseline geometrical model 50 correspondingly consists of seven rows R1-R7 of baseline model markers 51 extending between a proximal end and a distal end of baseline geometrical model 50.

Figure 5D:
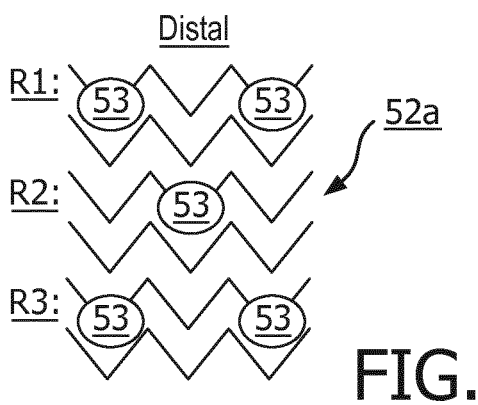
Figure 5C:
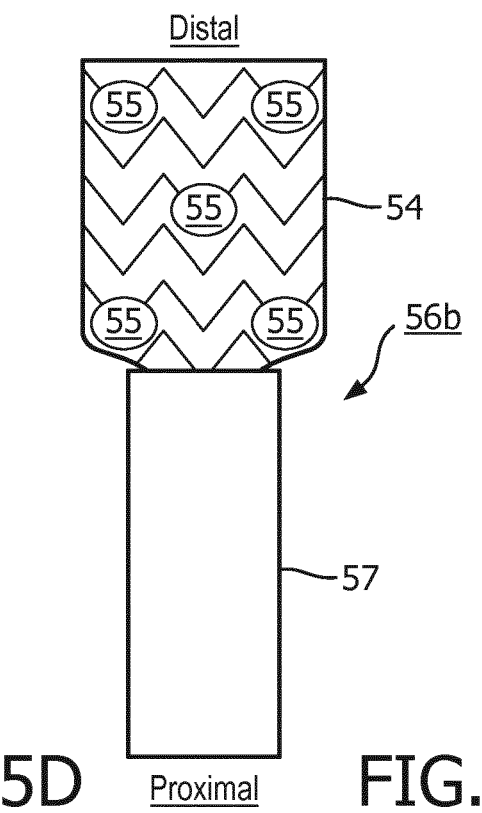

For this exemplary scenario, as illustrated in FIG. 5C, a non-torsional partial unsheathing 56b of a first three (3) distal rows R1-R3 of endograft 54 as covered by a catheter 57 occurs as endograft 54 is transitioned from an undeployed state (an initial pre-deployed state) to a semi-deployed state (an initial post-deployed state). FIG. 5D illustrates an imaged geometrical model 52a of imaged model markers 53 digitally constructed from an extravascular imaging or an intravascular imaging of non-torsional partial unsheathing 56b of the first three (3) distal rows R1-R3 of endograft 54 as shown in FIG. 5C. For this partial unsheathing of endograft 54, a matrix orientation of imaged geometrical model 52a of imaged model markers 53 of rows R1-R3 relative to a longitudinal axis of endograft 54 is identical to a matrix orientation of baseline geometrical model 50 of baseline model markers 51 of rows R1-R3 relative to the longitudinal axis of endograft 54.

Motion vectors are computed between registered pairs of baseline model markers 51 and imaged model markers 53 of rows R1-R3, and the computed motion vectors are compared in terms of direction and/or magnitude to thereby determine any torqueing of endograft 54.

Figure 6A:
FIGS. 6A-6D illustrate zero and non-zero motion vectors indicative of the non-torsional deployment of the endograft shown in FIGS. 5A-5D.
Figure 6A:
Figure 6A:

For example, FIG. 6A illustrates zero motion vectors 59 computed for registered pairs of baseline model markers 51 and imaged model markers 53 of rows R1-R3 whereby the zero motion vectors 59 indicate a non-torsional, non-rotational deployment 58a of endograft 54 from the undeployed state (the initial pre-deployed state) to the semi-deployed state (the initial post-deployed state) based on a matrix orientation similarity of models 50 and 52a relative to the longitudinal axis of endograft 54.

Figure 6B:
Figure 6B:
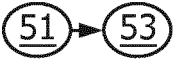
Figure 6B:

By further example, FIG. 6B illustrates identical non-zero motion vectors (symbolized by arrows) computed for registered pairs of baseline model markers 51 and imaged model markers 53 of rows R1-R3 whereby a direction and a magnitude of the identical non-zero motion vectors indicate a non-torsional, symmetrical rotational deployment 58*b* of endograft 54 from the undeployed state (the pre-deployed state) to the semi-deployed state (the post-deployed state) based on a matrix orientation similarity of models 50 and 52*a* relative to the longitudinal axis of endograft 54. While not indicative of a torqueing of endograft 54, the symmetrical rotation is of importance to note in terms of any axial misalignment of the endograft within a vascular anatomy.

Further for this exemplary scenario, a non-torsional complete unsheathing of the seven (7) rows R1-R7 of endograft 54 as covered by catheter 57 occurs as endograft 54 is transitioned from the semi-deployed state (a final pre-deployed state) as shown in FIG. 5C to a fully deployed state (a final post-deployed state) as shown in FIG. 5D. Imaged geometrical model 52*a* of imaged model markers 53 is again digitally constructed from an extravascular imaging or an intravascular imaging of the non-torsional complete sheathing of the seven (7) rows R1-R7 of endograft 54, and the constructed imaged geometrical model 52*a* is identical to baseline geometrical model 50. For this complete unsheathing of endograft 54, a matrix orientation of imaged geometrical model 52*a* of imaged model markers 53 of rows R1-R7 relative to a longitudinal axis of endograft 54 is identical to a matrix orientation of baseline geometrical model 50 of baseline model markers 51 of rows R1-R7 relative to the longitudinal axis of endograft 54.

Again, motion vectors are computed between registered pairs of baseline model markers 51 and imaged model markers 53 of rows R1-R7, and the computed motion vectors are compared in terms of direction and/or magnitude to thereby determine any twisting of endograft 54.

Figure 6C:
Figure 6C:
Figure 6C:
Figure 6C:
Figure 6C:
Figure 6C:
Figure 6C:

For example, FIG. 6C illustrates zero motion vectors 59 computed for registered pairs of baseline model markers 51 and imaged model markers 53 of rows R1-R7 whereby the zero motion vectors 59 indicate a non-torsional, non-rotational deployment 58*c* of endograft 54 from the undeployed state (the initial pre-deployed state) to a fully deployed state (the final post-deployed state) based on a matrix orientation similarity of models 50 and 52 relative to the longitudinal axis of endograft 54.

Figure 6D:
Figure 6D:
Figure 6D:
Figure 6D:
Figure 6D:
Figure 6D:
Figure 6D:

By further example, FIG. 6D illustrates identical non-zero motion vectors (symbolized by arrows) computed for registered pairs of baseline model markers 51 and imaged model markers 53 of rows R1-R7 whereby the identical non-zero motion vectors indicate a non-torsional, symmetrical rotational deployment 58*d* of endograft 54 from the undeployed state (the initial pre-deployed state) to a fully deployed state (the final post-deployed state) based on a matrix orientation similarity of models 50 and 52 relative to the longitudinal axis of endograft 54. Again, while not indicative of a torqueing of endograft 54, the symmetrical rotation is of importance to note in terms of any axial misalignment of the endograft within a vascular anatomy.

S46: Exemplary Detection of a Torsional Deployment of an Endograft.

Figure 5E:
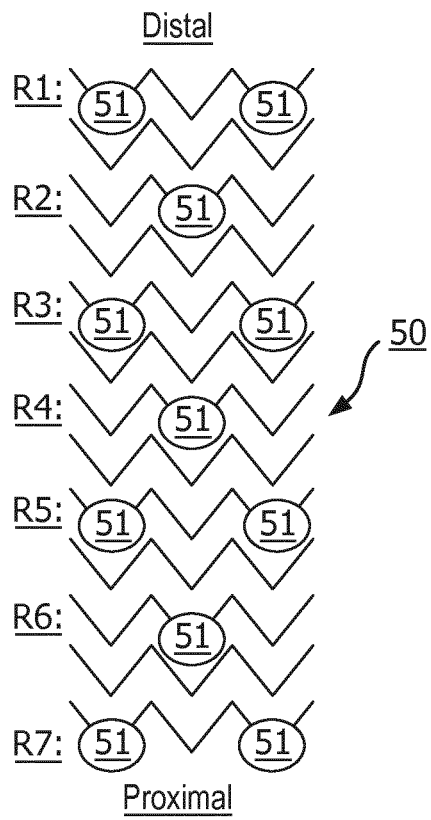
FIGS. 5E-5H illustrate a torsional deployment of an endograft as represented by the matrix of geometrical model of the endograft in accordance with the inventive principles of the present disclosure.

FIG. 5E illustrates a baseline geometrical model 50 digitally constructed from a device model, an extravascular imaging or an intravascular imaging of a fully expanded state 56*a* of endograft 54 as shown in FIG. 5B. Again, more particularly, endograft 54 consists of seven rows R1-R7 of imageable markers 55 extending between a proximal end and a distal end of endograft 54, and baseline geometrical model 50 correspondingly consists of seven rows R1-R7 of baseline model markers 51 extending between a proximal end and a distal end of baseline geometrical model 50.

Figure 5H:
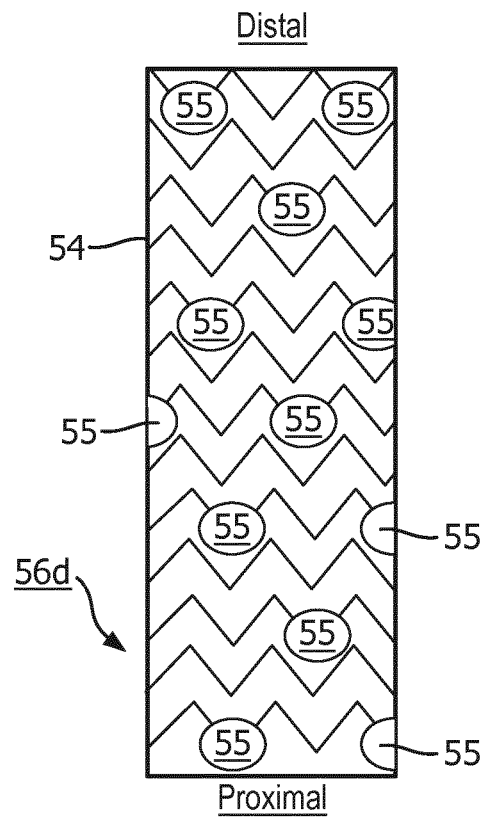
Figure 5G:
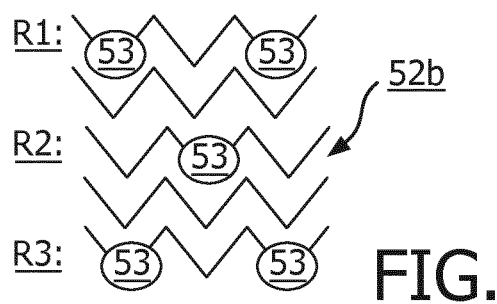
Figure 5F:
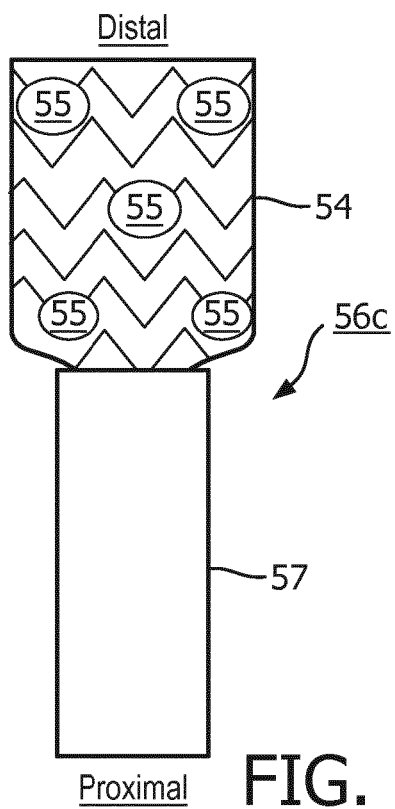

For this exemplary scenario, as illustrated in FIG. 5F, a torsional partial unsheathing 56*c* of a first three (3) distal rows R1-R3 of endograft 54 as covered by a catheter 57 occurs as endograft 54 is transitioned from an undeployed state (an initial pre-deployed state) to a semi-deployed state (an initial post-deployed state). FIG. 5G illustrates an imaged geometrical model 52*b* of imaged model markers 53 digitally constructed from an extravascular imaging or an intravascular imaging of the torsional partial unsheathing 56*c* of the first three (3) distal rows R1-R3 of endograft 54 as shown in FIG. 5F.

Motion vectors are computed between registered pairs of baseline model markers 51 and imaged model markers 53 of rows R1-R3, and the computed motion vectors are compared in terms of direction and/or magnitude to thereby determine any torqueing of endograft 54.

Figure 6E:
FIGS. 6E and 6F illustrate non-zero motion vectors indicative of the torsional deployment of the endograft shown in FIGS. 5E-5H.
Figure 6E:
Figure 6E:

For example, FIG. 6E illustrates zero motion vectors 59 computed for registered pairs of baseline model markers 51 and imaged model markers 53 of row R1, and further illustrates magnitude increasing non-zero motion vectors (symbolized by arrows) computed for registered pairs of baseline model markers 51 and imaged model markers 53 of rows R2 and R3 whereby the disparity between the zero motion vectors and the magnitude increasing vectors indicate a torsional deployment 58*e* of endograft 54 from the undeployed state (the initial pre-deployed state) to the semi-deployed state (the initial post-deployed state) based on a matrix orientation dissimilarity between models 50 and 52*b* relative to the longitudinal axis of endograft 54.

Further this exemplary scenario, a torsional complete unsheathing of the seven (7) rows R1-R7 of endograft 54 as covered by catheter 57 occurs as endograft 54 is transitioned from the semi-deployed state (a final pre-deployed state) as shown in FIG. 5F to a fully deployed state (a final post-deployed state) as shown in FIG. 5H. Imaged geometrical model 52*b* of imaged model markers 53 is again digitally constructed from an extravascular imaging or an intravascular imaging of the torsional complete sheathing of the seven (7) rows R1-R7 of endograft 54 (not shown). For this complete unsheathing of endograft 54, a matrix orientation of imaged geometrical model 52*a* of imaged model markers 53 of rows R1-R7 relative to a longitudinal axis of endograft 54 is different than a matrix orientation of baseline geometrical model 50 of baseline model markers 51 of rows R1-R7 relative to the longitudinal axis of endograft 54.

Again, motion vectors are computed between registered pairs of baseline model markers 51 and imaged model markers 53 of rows R1-R7, and the computed motion vectors are compared in terms of direction and/or magnitude to thereby determine any torqueing of endograft 54.

Figure 6F:
Figure 6F:
Figure 6F:
Figure 6F:
Figure 6F:
Figure 6F:
Figure 6F:

For example, FIG. 6F illustrates zero motion vectors 59 computed for registered pairs of baseline model markers 51 and imaged model markers 53 of row R1, and further illustrates magnitude increasing non-zero motion vectors (symbolized by arrows) computed for registered pairs of baseline model markers 51 and imaged model markers 53 of rows R2-R7 whereby the disparity between the zero motion vectors and the magnitude increasing vectors indicate a torsional deployment 58*f* of endograft 54 from the semi-deployed state (the final pre-deployed state) to the fully deployed state (the final post-deployed state) based on a matrix orientation dissimilarity between models 50 and 52*b* relative to the longitudinal axis of endograft 54.

S46: Exemplary Detection of a Non-Torsional Deployment of a Stent.

Figure 7A:
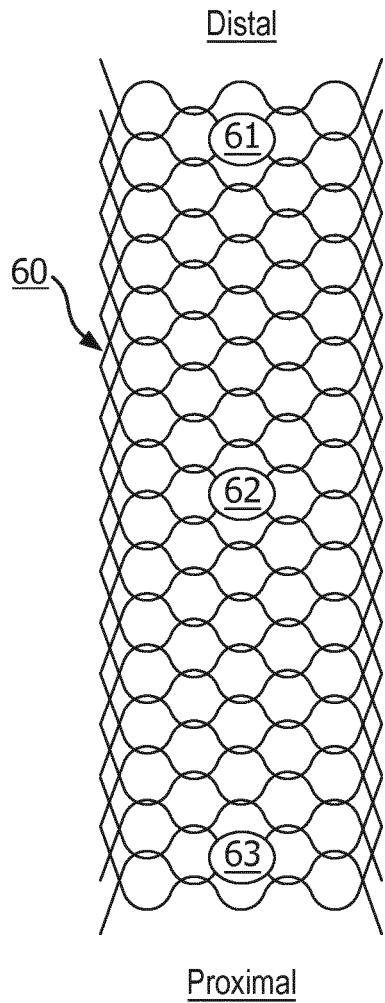
FIGS. 7A-7D illustrate a non-torsional deployment of a stent as represented by the matrix of geometrical model of the endograft in accordance with the inventive principles of the present disclosure.
Figure 7B:
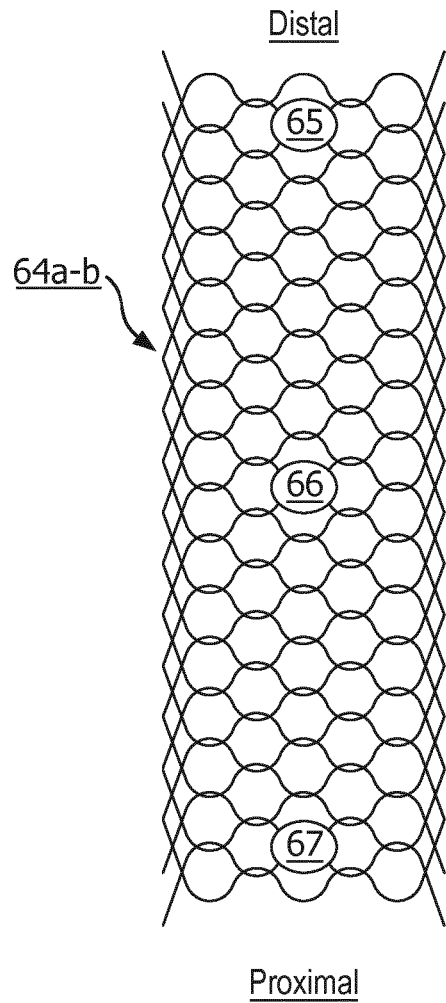

FIG. 7A illustrates a baseline geometrical model 60 digitally constructed from a device model, an extravascular imaging or an intravascular imaging of a fully expanded state 64b of a stent 64 as shown in FIG. 7B. More particularly, stent 64 consists of a column of imageable markers 65-67 longitudinally extending between a proximal end and a distal end of stent 64, and baseline geometrical model 60 correspondingly consists of a column of baseline model markers 61-63 longitudinally extending between a proximal end and a distal end of baseline geometrical model 60.

Figure 7C:
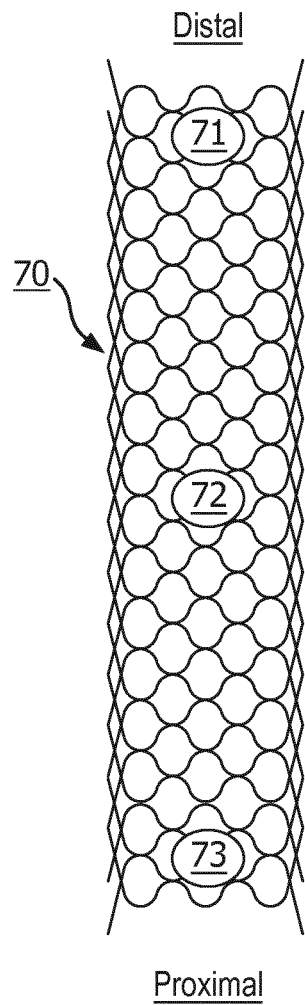
Figure 7D:
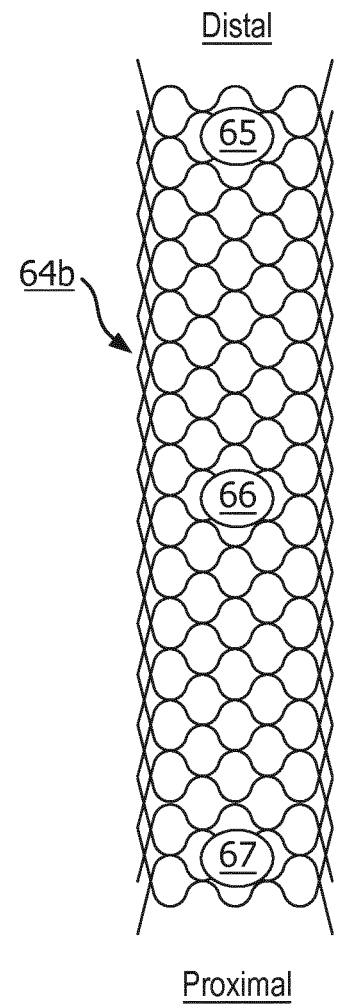

For this exemplary scenario, FIG. 7D illustrates a non-torsional partial expansion 64a of stent 64 as stent 64 is transitioned from an undeployed state (an initial pre-deployed state) to a semi-deployed state (an initial post-deployed state). FIG. 7C illustrates an imaged geometrical model 70 of imaged model markers 71-73 digitally constructed from an extravascular imaging or an intravascular imaging of non-torsional partial expansion 64a of stent 64 as shown in FIG. 7D. For this non-torsional partial expansion 64a of stent 64, a matrix orientation of imaged geometrical model 70 of imaged model markers 71-73 relative to a longitudinal axis of stent 64 is identical to a matrix orientation of baseline geometrical model 60 of baseline model markers 61-63 relative to the longitudinal axis of stent 64.

Angular vectors are computed between registered pairs of baseline model markers 61-63 and imaged model markers 71-73, and the computed angular vectors are compared in terms of direction and/or magnitude to thereby determine any torqueing of stent 64.

Figure 8A:
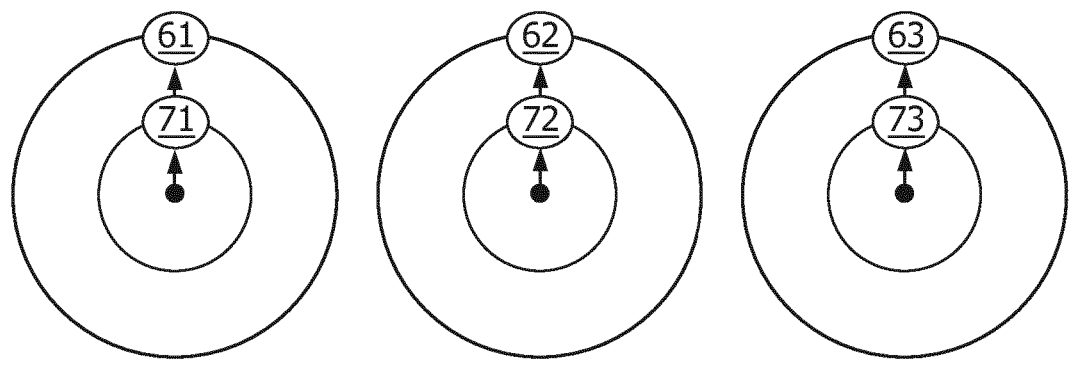
FIGS. 8A and 8B illustrate zero angular vectors indicative of the non-torsional deployment of the endograft shown in FIGS. 7A-7D.

For example, FIG. 8A illustrates baseline model markers 61-63 and imaged model markers 71-73 radially extending in an identical direction from a longitudinal axis of stent 64. Thus, while the magnitude of radial extension is different between baseline model markers 61-63 and imaged model markers 71-73, the zero angular vectors (symbolized by arrows) computed for registered pairs of baseline model markers 61-63 and imaged model markers 71-73 indicate a non-torsional, non-rotational deployment 68a of stent 64 from the undeployed state (the initial pre-deployed state) to the semi-deployed state (the initial post-deployed state) based on a matrix orientation similarity of models 60 and 70 relative to the longitudinal axis of stent 64.

Further for this exemplary scenario, FIG. 7B illustrates a non-torsional complete expansion 64a of stent 64 as stent 64 is transitioned from the semi-deployed state (a final pre-deployed state) to a fully deployed state (a final post-deployed state). Again, angular vectors are computed between registered pairs of baseline model markers 61-63 and imaged model markers 71-73, and the computed angular vectors are compared in terms of direction and/or magnitude to thereby determine any torqueing of stent 64.

Figure 8B:
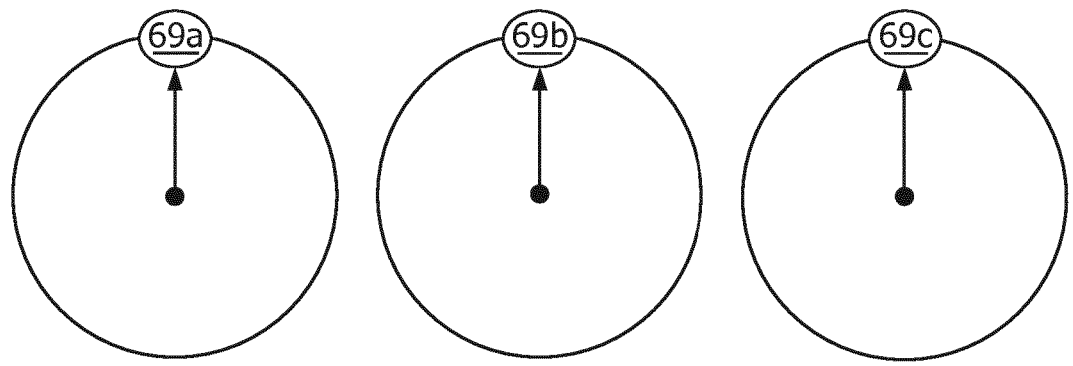

For example, FIG. 8B illustrates baseline model markers 61-63 and imaged model markers 71-73 radially extending in an identical direction and equal magnitude from a longitudinal axis of stent 64. Thus, zero angular vector 69a-c computed for registered pairs of baseline model markers 61-63 and imaged model markers 71-73 indicate a non-torsional, non-rotational deployment 68a of stent 64 from the semi-deployed state (a final pre-deployed state) to a fully deployed state (a final post-deployed state) based on a matrix orientation similarity of models 60 and 70 relative to the longitudinal axis of stent 64.

S46: Exemplary Detection of a Torsional Deployment of a Stent.

As previously described, FIG. 7A illustrates a baseline geometrical model 60 digitally constructed from a device model, an extravascular imaging or an intravascular imaging of a fully expanded state 64b of a stent 64 as shown in FIG. 7B. Again, more particularly, stent 64 consists of a column of imageable markers 65-67 longitudinally extending between a proximal end and a distal end of stent 64, and baseline geometrical model 60 correspondingly consists of a column of baseline model markers 61-63 longitudinally extending between a proximal end and a distal end of baseline geometrical model 60.

Figure 7E:
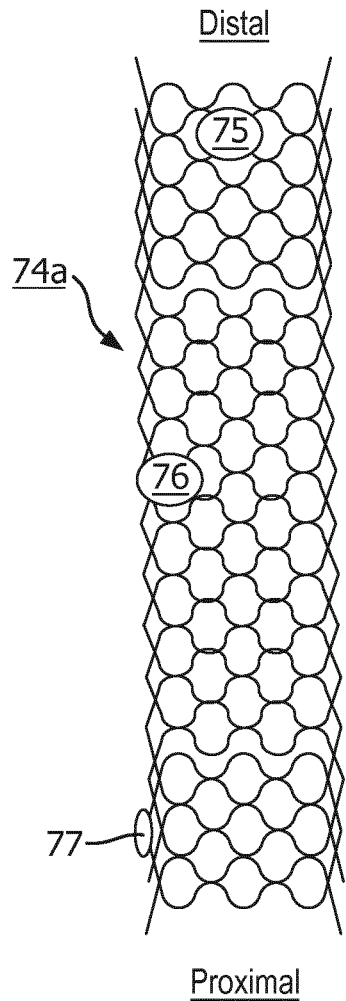
FIGS. 7E-7H illustrate a torsional deployment of a stent as represented by the matrix of geometrical model of the endograft in accordance with the inventive principles of the present disclosure.
Figure 7F:
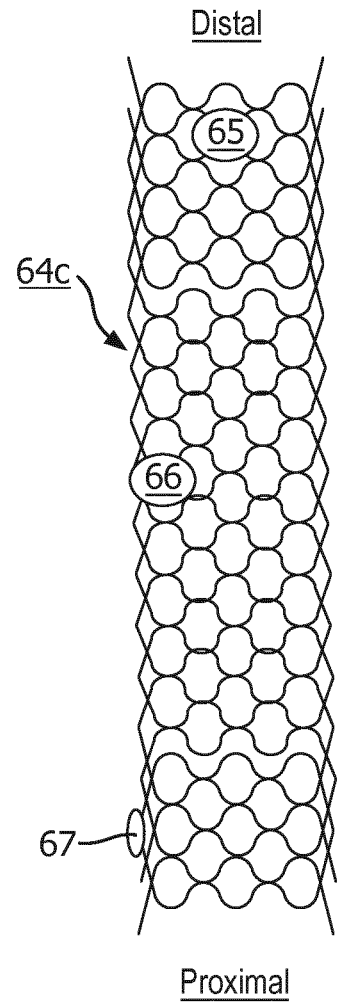
Figure 7G:
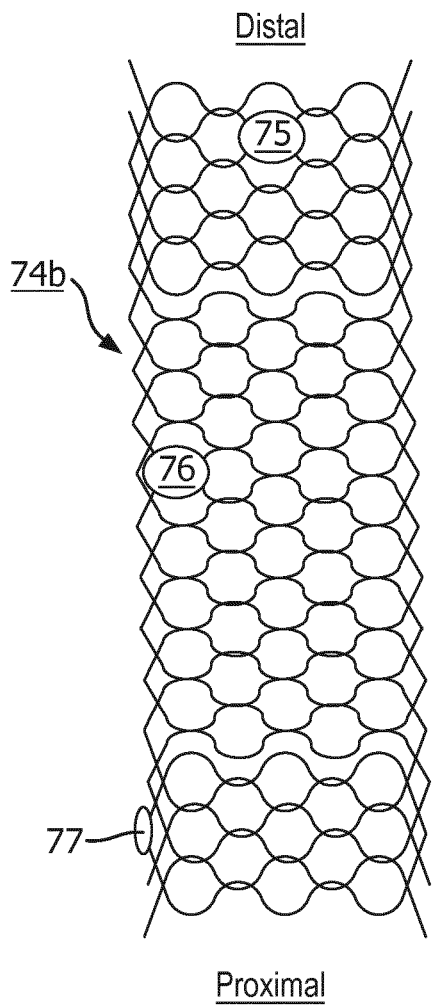

For this exemplary scenario, FIG. 7F illustrates a torsional partial expansion 64c of stent 64 as stent 64 is transitioned from an undeployed state (an initial pre-deployed state) to a semi-deployed state (an initial post-deployed state). FIG. 7E illustrates an imaged geometrical model 74 of imaged model markers 75-77 digitally constructed from an extravascular imaging or an intravascular imaging of torsional partial expansion 64c of stent 64 as shown in FIG. 7F. For this torsional partial expansion 64c of stent 64, a matrix orientation of imaged geometrical model 74a of imaged model markers 75-77 relative to a longitudinal axis of stent 64 is identical to a matrix orientation of baseline geometrical model 60 of baseline model markers 61-63 relative to the longitudinal axis of stent 64.

Angular vectors are computed between registered pairs of baseline model markers 61-63 and imaged model markers 75-77, and the computed angular vectors are compared in terms of direction and/or magnitude to thereby determine any torqueing of stent 64.

Figure 8C:
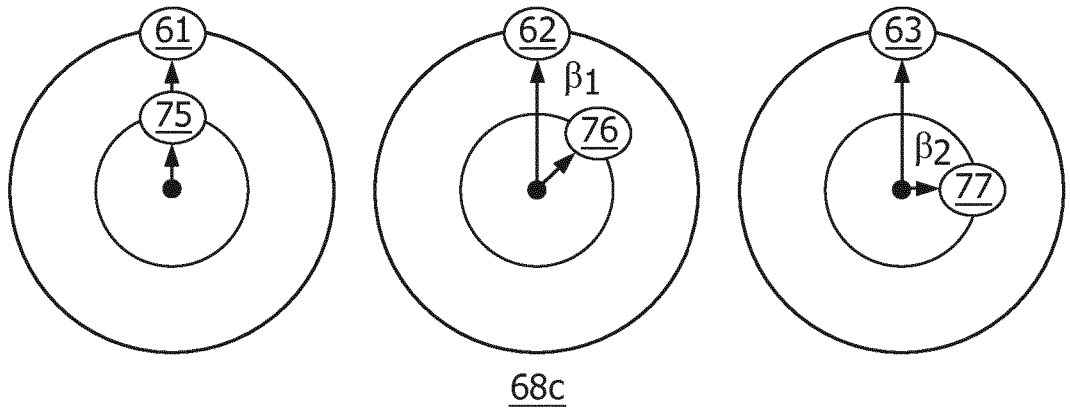
FIGS. 8C and 8D illustrates non-zero angular vectors indicative of the torsional deployment of the stent shown in FIGS. 7E-7H.

For example, FIG. 8C illustrates baseline model markers 61-63 and imaged model markers 75-77 radially extending in different directions and unequal magnitudes from a longitudinal axis of stent 64. The non-zero angular vectors (symbolized by $\beta_1$ and $\beta_2$) computed for registered pairs of baseline model markers 62 and 63 and imaged model markers 76 and 77 indicate a torsional deployment 68a of stent 64 from the undeployed state (the initial pre-deployed state) to the semi-deployed state (the initial post-deployed state) based on a matrix orientation dissimilarity of models 60 and 70 relative to the longitudinal axis of stent 64.

Figure 7H:
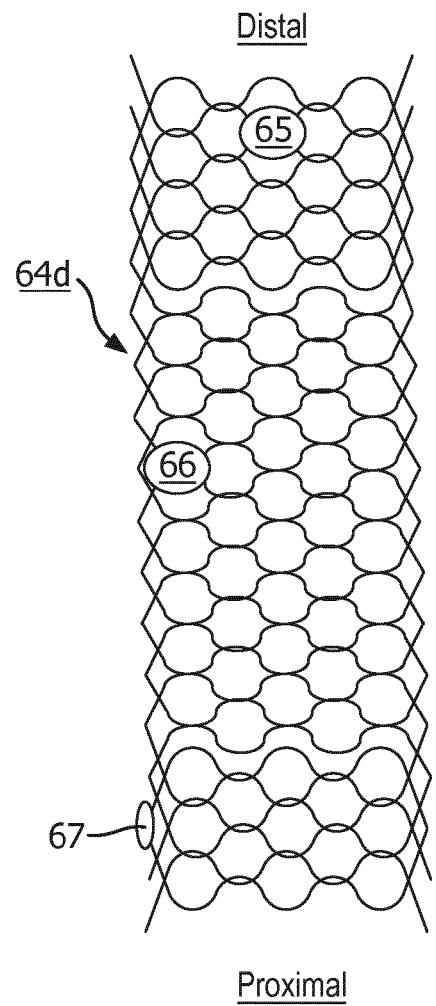

Further for this exemplary scenario, FIG. 7H illustrates a torsional complete expansion 64c of stent 64 as stent 64 is transitioned from the semi-deployed state (a final pre-deployed state) to a fully deployed state (a final post-deployed state). Again, angular vectors are computed between registered pairs of baseline model markers 61-63 and imaged model markers 75-77, and the computed angular vectors are compared in terms of direction and/or magnitude to thereby determine any torqueing of stent 64.

Figure 8D:
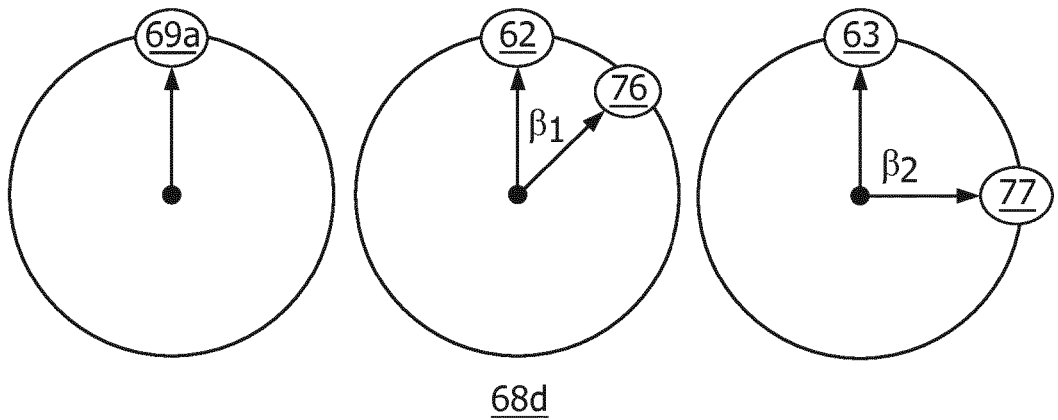

For example, FIG. 8D illustrates baseline model markers 61-63 and imaged model markers 75-77 radially extending in different directions and equal magnitude from a longitudinal axis of stent 64. The non-zero angular vectors (symbolized by $\beta_1$ and $\beta_2$) computed for registered pairs of baseline model markers 62 and 63 and imaged model markers 76 and 77 indicate a torsional deployment 68a of stent 64 from the semi-deployed state (a final pre-deployed state) to a fully deployed state (a final post-deployed state) based on a matrix orientation dissimilarity of models 60 and 70 relative to the longitudinal axis of stent 64.

Referring back to FIG. 4, stage S46 of flowchart 40 may further encompass an activation of any visual, audible and/or mechanical alerts of a detection of a torsional deployment of the vascular therapy device to the post-deployed state of stage S44.

In one embodiment, non-zero motion vectors or non-zero angular vectors may be displayed to visualize a detection of any torsional deployment of the vascular therapy device. More particularly, non-zero motion vectors or non-zero angular vectors may be displayed to visualize a detection of an unacceptable torsional deployment of the vascular therapy device based on the non-zero motion vectors or the non-zero angular vectors exceed a magnitude threshold and/or a direction threshold representative of a significant torqueing of the vascular therapy device.

In a second embodiment, a displayed image of the vascular therapy device may turn colors and/or flash to visualize a detection of any torsional deployment of the vascular therapy device. More particularly, the displayed image of the vascular therapy device may turn colors and/or flash to visualize a detection of an unacceptable torsional deployment of the vascular therapy device based on the non-zero motion vectors or the non-zero angular vectors exceed a magnitude threshold and/or a direction threshold representative of a significant torqueing of the vascular therapy device.

In a third embodiment, an audible warning (e.g., speech or horn) may be activated to communicate a detection of any torsional deployment of the vascular therapy device. More particularly, the audible warning may be activated to communicate a detection of an unacceptable torsional deployment of the vascular therapy device based on the non-zero motion vectors or the non-zero angular vectors exceed a magnitude threshold and/or a direction threshold representative of a significant torqueing of the vascular therapy device.

In a fourth embodiment, if applicable, a robot controlling a navigation of the vascular therapy device through a vascular anatomy may be disabled upon a detection of any torsional deployment of the vascular therapy device. More particularly, such a robot may be disabled upon a detection of an unacceptable torsional deployment of the vascular therapy device based on the non-zero motion vectors or the non-zero angular vectors exceed a magnitude threshold and/or a direction threshold representative of a significant torqueing of the vascular therapy device.

To facilitate a further understanding of the present disclosure, exemplary embodiments of a torque detection vascular therapy system of the present disclosure for executing a torque detection vascular therapy method of the present invention during an endovascular procedure will now be described in connection with FIGS. 9-11B. From the description of FIGS. 9-11B, those having ordinary skill in the art will understand how to make and use additional varied and numerous embodiments of a torque detection vascular therapy system in accordance with the present disclosure.

Figure 9:
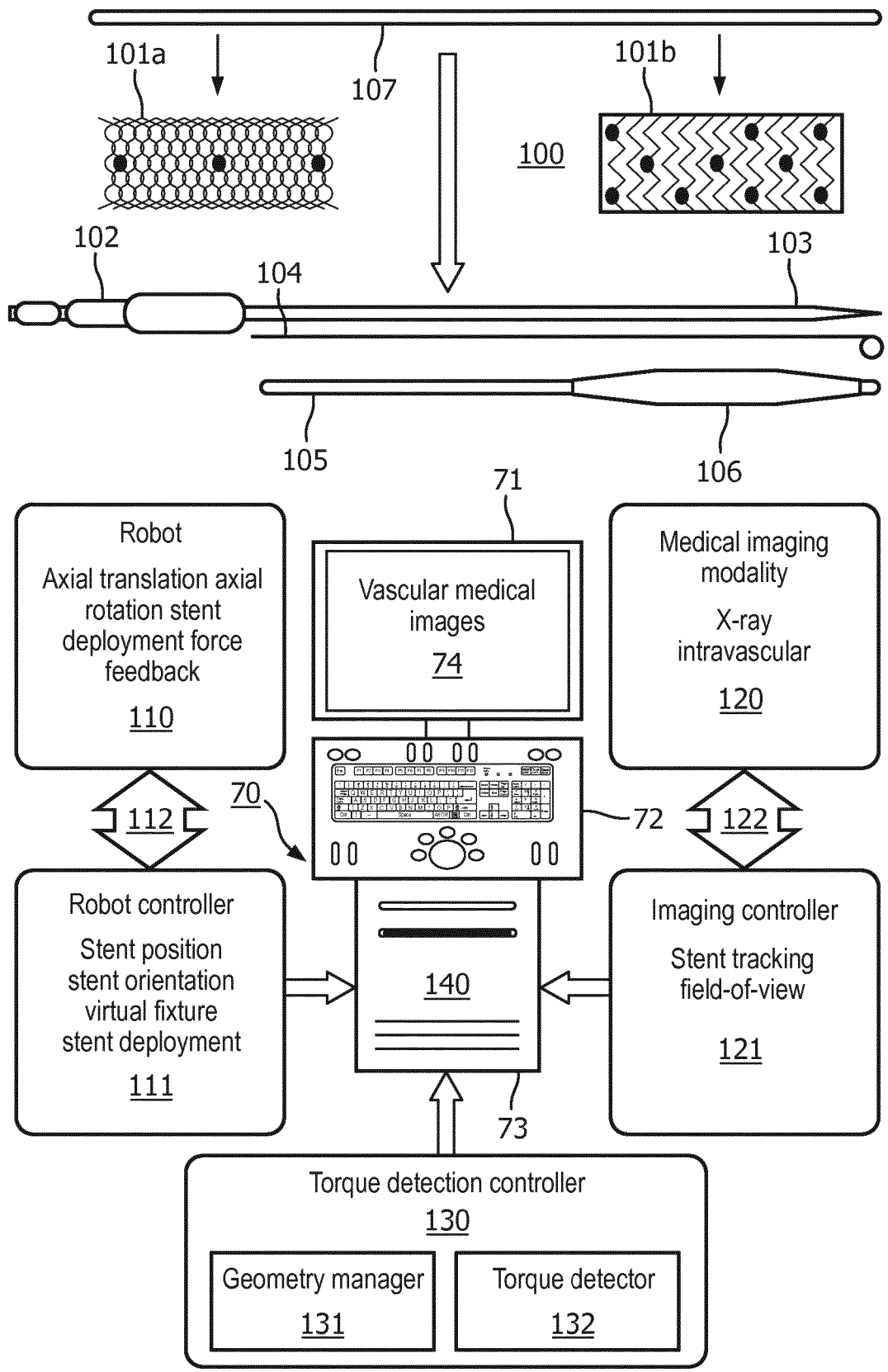
FIG. 9 illustrates an exemplary embodiment of a torque detection vascular therapy system in accordance with the inventive principles of the present disclosure.

Referring to FIG. 9, a torque detection vascular therapy system of the present disclosure employs:

(1) a vascular therapy deployment device 100 assembled from
  (a) vascular therapy devices the form of a stent 101a and an endograft 101b, each having a matrix of imageable markers,
  (b) a proximal control 102,
  (c) delivery tools in the form of a sheath catheter 103, a guidewire 104, and/or a catheter 105 having a balloon 106, and
  (d) one or more optical shape sensors 107;
(2) a robot 110 (which may be omitted for manual control);
(3) a medical imaging modality 120; and
(4) a vascular therapy workstation 140 configured with a robot controller 111, an imaging controller 121 and a torque detection controller 130.

Optical shape sensor ("OSS") 107 uses light along one or more optical fibers for device localization and navigation during an endovascular procedure. An operating principle of OSS sensor 107 involves use of distributed strain measurement in the optical fiber including, but not limited to, use of characteristic Rayleigh backscatter or use of controlled grating patterns. A shape along the optical fiber begins at a specific point along OSS 107 associated with an origin of an OSS coordinate system (not shown) whereby a subsequent shape position and orientation of OSS 107 are relative to the origin of OSS coordinate system.

In order to introduce the use of OSS 107 into the endovascular procedure for supporting an image guidance stent 101a/endograft 101b, in practice OSS 107 may integrated into the endograft development in accordance with various approaches as known in the art of the present disclosure including, but not limited to:

(1) an integration of OSS 107 into stent 101a/endograft 101b;
(2) discrete points of attachment of OSS 107 onto stent 101a/endograft 101b;
(3) integration of OSS 107 into a wall of catheters 103 and 105;
(4) attachment of OSS 107 to a handle of proximal control 41; and
(5) integration of OSS 107 into the guidewire 104.

Image rendering and image modeling of stent 101a/endograft 101b may be generated based on the optical shape sensing information in dependence upon the integration method.

Robot 110 may be attached to proximal control 102 for navigating stent 101a/endograft 101b within a vascular anatomy (e.g., an abdominal aorta) via one of the delivery tools. In practice of the present disclosure, an attachment of robot 110 to proximal control 102 and/or delivery tool 42 includes, but is not limited to:

(1) a clamping of robot onto a torsional component of stent 101a/endograft 101b coupled to a delivery tool;
(2) a use of a mating piece between stent 101a/endograft 101b and robot 110; and
(3) a passing of sheath catheter 103 through a collet attached to robot 110.

In one embodiment, robot 110 an axial rotation and/or an axial translation of stent 101a/endograft 101b relative to a robot coordinate system as known in the art of the present disclosure. For this embodiment, if OSS sensor 107 is utilized, the OSS coordinate system associated with OSS senor 107 may be spatially registered to the robot coordinate system of robot 110 as known in the art of the present disclosure.

A key feature of robot 110 is the ability to hold stent 101a/endograft 101b in a stable position/orientation that reduces a need for an operator to be holding a handle of proximal control 120 in position/orientation at all times. In the event that stent 101a/endograft 101b does slip while being navigated and/or positioned within the vascular anatomy, robot 110 may automatically attempt to reposition/reorient stent 101a/endograft 101b within the vascular anatomy or can warn the operator of workstation 140. In addition, by incorporating force sensor(s) as known in the art of the present disclosure, forces required to insert stent 101a/endograft 101b into the abdominal aorta may be measured and force(s) required to hold stent 101a/endograft 101b during vessel cannulation, etc., may also be measured. Such force readings could be used to warn the operator of workstation 140 if excessive forces were applied to the patient.

Still referring to FIG. 9, medical imaging modality 120 may be any known imaging modality as known in the art of the present disclosure for an extravascular imaging of stent 101a/endograft 101b (e.g., an X-ray modality) and/or an intravascular imaging of stent 101a/endograft 101b (e.g, optical coherence tomography, near infra-red imaging, IVUS, etc.). For the imaging, if OSS sensor 107 is utilized, the OSS coordinate system associated with OSS senor 107 may be spatially registered with an image coordinate system of imaging modality 120 as known in the art of the present disclosure or to landmarks/targets identifiable in X-ray images whereby the shape sensing data of OSS 107 is spatially registered to any medical image generated from the X-ray imaging for robotic control purposes.

Still referring to FIG. 9, vascular therapy workstation 140 employs a monitor 141, an interface platform 142 and a workstation computer 143.

Workstation computer 143 is connected/coupled to OSS 107, if utilized, and imaging modality 120 to respectively input shape sensing data and imaging data as known in the art of the present disclosure. More particularly, for the input of shape sensing data, a light detector (not shown) as known in the art of the present disclosure for detecting light reflected by and/or transmitted through OSS 107 may be internal or external to workstation computer 73.

In practice of the present disclosure, as installed on workstation computer 143, robot controller 111, imaging controller 121, torque detection controller 130 and any additional controllers not shown (e.g., a display controller) may be segregated as shown, or partially or wholly integrated. Also in practice, torque detection controller 130 may be installed in an additional workstation (not shown)(e.g., a laptop or a pad) and remotely connected to workstation computer 73.

Still referring to FIG. 9, each controller 111, 121 and 130 includes processor(s), memory, a user interface, a network interface, and a storage interconnected via one or more system buses.

Each processor may be any hardware device, as known in the art of the present disclosure or hereinafter conceived, capable of executing instructions stored in memory or storage or otherwise processing data. In a non-limiting example, the processor may include a microprocessor, field programmable gate array (FPGA), application-specific integrated circuit (ASIC), or other similar devices.

The memory may include various memories, as known in the art of the present disclosure or hereinafter conceived, including, but not limited to, L1, L2, or L3 cache or system memory. In a non-limiting example, the memory may include static random access memory (SRAM), dynamic RAM (DRAM), flash memory, read only memory (ROM), or other similar memory devices.

The user interface may include one or more devices, as known in the art of the present disclosure or hereinafter conceived, for enabling communication with a user such as an administrator. In a non-limiting example, the user interface may include a command line interface or graphical user interface that may be presented to a remote terminal via the network interface.

The network interface may include one or more devices, as known in the art of the present disclosure or hereinafter conceived, for enabling communication with other hardware devices. In an non-limiting example, the network interface may include a network interface card (NIC) configured to communicate according to the Ethernet protocol. Additionally, the network interface may implement a TCP/IP stack for communication according to the TCP/IP protocols. Various alternative or additional hardware or configurations for the network interface will be apparent.

The storage may include one or more machine-readable storage media, as known in the art of the present disclosure or hereinafter conceived, including, but not limited to, read-only memory (ROM), random-access memory (RAM), magnetic disk storage media, optical storage media, flash-memory devices, or similar storage media. In various non-limiting embodiments, the storage may store instructions for execution by the processor or data upon with the processor may operate. For example, the storage may store a base operating system for controlling various basic operations of the hardware. The storage also stores application modules in the form of executable software/firmware for implementing the various functions of the controllers as further described in the present disclosure.

Still referring to FIG. 9, in one embodiment, robot controller 111 includes application modules (not shown) for a positioning, orienting, virtual fixture and deployment of stent 101a/endograft 101b within a vascular anatomy as known in the art of the present disclosure, and imaging controller 121 include application modules (not shown) for visually tracking the positioning, orienting, virtual fixture and deployment of stent 101a/endograft 101b within the vascular anatomy from adjustable field-of-views as known in the art of the present disclosure.

In practice of the present disclosure, robot controller 11 is connected to actuator controls of robot 110 for signal/data/command communication 112 between robot 110 and robot controller 111 including, but not limited to, actuation commands/signals from robot controller 111 to robot 110 and actuation data from robot 110 to robot controller 111 (e.g., a degree of axial translation and/or axial rotation of stent 101a/endograft 101b and any force feedback). Concurrently, imaging controller 121 is connected to imaging modality 120 for signal/data/command communication 122 between imaging modality 120 and imaging controller 121 including, but not limited to, imaging data from imaging modality 120 to imaging controller 121 and actuation commands/signals from imaging controller 121 to imaging modality 120.

Still referring to FIG. 9, torque detection controller 120 includes application modules in the form of a geometry manager 131 for executing stages S42 and S44 of flowchart 40 (FIG. 4) as previously described in the present disclosure and a torque detector 132 for executing stage 46 of flowchart 40 as previously described in the present disclosure.

In practice of the present disclosure, embodiments of geometry manager 131 and torque detector 132 are configured in accordance with which particular vascular therapy device 101a and 101b is being monitored, which delivery device(s) 102-106 is(are) being employed, whether or not OSS sensor 107 is being utilized and the form of imaging modality 120.

To facilitate a further understanding of geometry manager 131 and torque detector 132, the following are descriptions of an exemplary extravascular imaging of an endovascular procedure and an exemplary intravascular imaging of endovascular procedure.

Extravascular X-Ray Imaging.

Figure 10A:
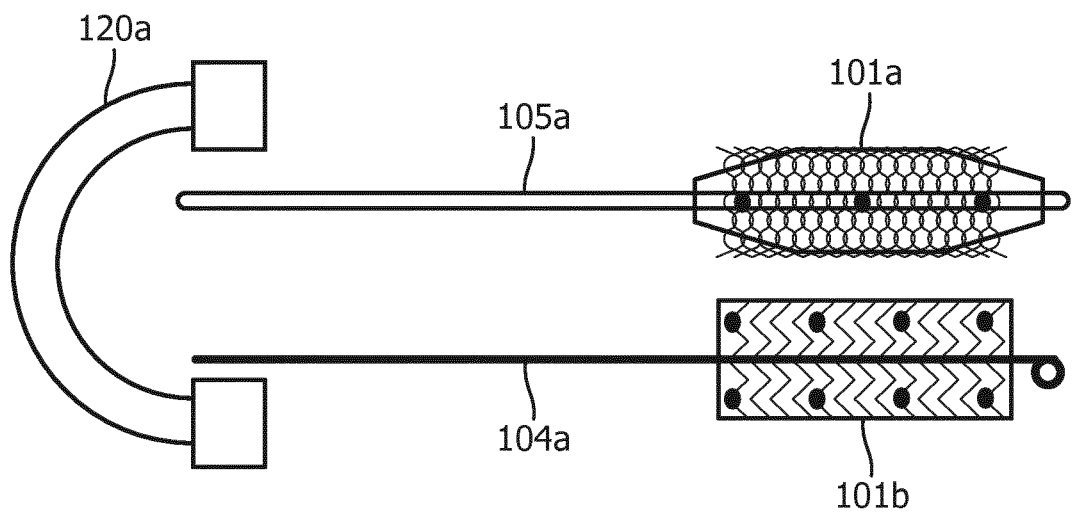
FIGS. 10A and 10B illustrate an exemplary X-ray imaging of a vascular therapy device in accordance with the inventive principles of the present disclosure.

FIG. 10A illustrates an X-ray arm 120a operable for imaging a delivery and a deployment of stent 101a within a vascular anatomy via OSS balloon catheter 105a and for imaging a delivery and a delivery and a deployment of endograft 101b within a vascular anatomy via catheter OSS guidewire 104a.

During the endovascular procedure, generally automatically detecting a non-torsional deployment or a torsional deployment of stent 101*a*/endograft 101*b* involves:

(1) An operation of geometry manager 131 to pre-operatively reconstruct a baseline geometry model of stent 101*a*/endograft 101*b* from a device model in accordance with the present disclosure as previously described herein;

(2) Semi-deploying stent 101*a*/endograft 101*b* via robot 110 at targeted location within a vascular anatomy as known in the art of the present disclosure;

(3) An operation of geometry manager 131 to detect radiopaque markers of 101*a*/endograft 101*b* under imaging X-ray imaging in accordance with the present disclosure as previously described herein;

(4) An operation of geometry manager 131 to intra-operatively reconstruct a 3D geometrical model of stent 101*a*/endograft 101*b* from the imaged radiopaque markers of 101*a*/endograft 101*b* in accordance with the present disclosure as previously described herein;

(5) An optional operation of geometry manager 131 to modify the baseline geometry model based on intraoperative reconstruction of the imaged geometry model of stent 101*a*/endograft 101*b* in accordance with the present disclosure as previously described herein;

(6) An operation of geometry manager 131 to save a present configuration of stent 101*a*/endograft 101*b* as a reference (position, orientation, and deformation) by registering to the X-ray modality 120*a*;

(7) As stent 101*a*/endograft 101*b* is further deployed and new images are acquired, an operation of geometry manager 131 the displacement of the radiopaque markers of stent 101*a*/endograft 101*b* in accordance with the present disclosure as previously described herein;

(8) An optional operation of torque detector 132 to control a display of a directionality of radiopaque markers of stent 101*a*/endograft 101*b* over time; and (9) If the directionality manifests in adverse components (i.e., a matrix dissimilarity between the baseline geometrical model and the imaged geometrical mode as in accordance with the present disclosure as previously described herein), then torque detector 132 activates an alert to the operator of X-ray modality 120*a* of a detected torsional deployment of stent 101*a*/endograft 101*b*.

More particularly, the directionality of stent 101*a*/endograft 101*b* deformation is readily determined by torque manager 132, because the longitudinal direction of the stent 101*a*/endograft 101*b* is known from OSS 107 embedded within balloon catheter 105*a* or guidewire 104*a*. Specifically, a local z-axis stent 101*a*/endograft 101*b* is chosen such that it aligns with a vector from the proximal end of stent 101*a*/endograft 101*b* to a distal end stent 101*a*/endograft 101*b*, whose positions are known to torque manager 132 given by the registration of Step (6) above. The x- and y-axes are perpendicular to the z-axis and their specific alignment is immaterial for the present disclosure, because any convenient orientation may be chosen, such as, for example, x may extend along the image plane, and y may extend out of the image plane. A coordinate system of stent 101*a*/endograft 101*b* is thus expressed in terms of the shape coordinate system as $^{d}T_s$.

Figure 10B:
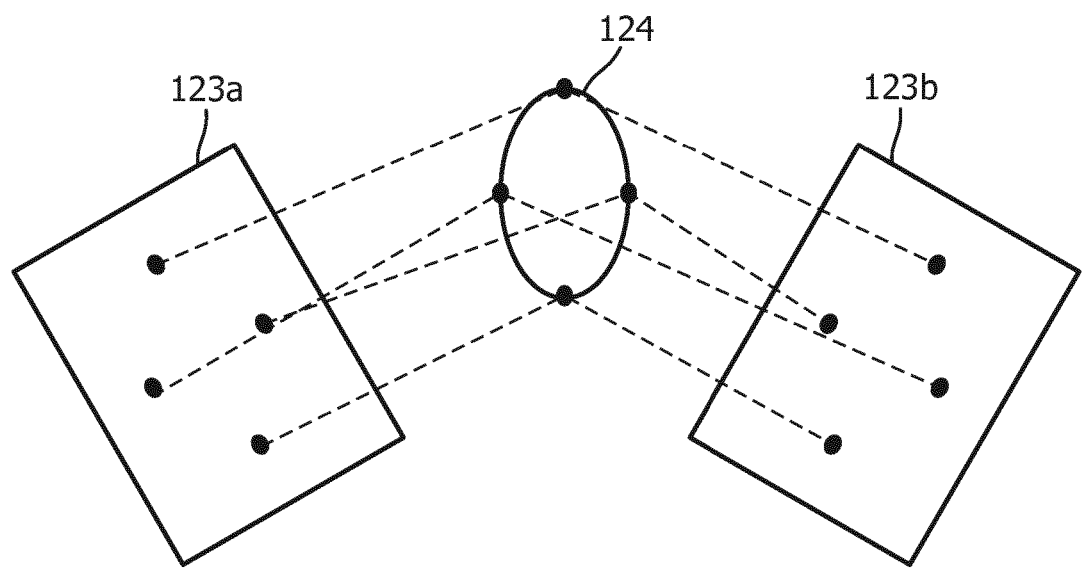

The 3D position of each radiopaque marker is computed per Step (4) above as exemplary shown in FIG. 10B illustrating an exemplary reconstruction of row of radiopaque markers 124 from two (2) X-ray images 123*a* and 123*b*, and repeated for each X-ray image acquired. From multiple X-ray images, a motion vector for each radiopaque marker is computed by torque manager 132 as the difference in tracked positions as previously described in the present disclosure. Because the stent 101*a*/endograft 101*b* is registered to the shape coordinate system, the motion vectors are also expressed in the shape coordinate system as $^{v}T_s$.

In one embodiment, the following equation [1] is executed torque manager 132 to obtain the motion vectors expressed in device coordinates:

$$^{d}T_v = {}^{d}T_s \cdot {}^{v}T_s^{-1} \quad [1]$$

For each motion vector $v=(v_x, v_y, v_z)$ expressed in device coordinates, the z-axis, or longitudinal rotation, or torsion, is computed by torque manager 132 in accordance with the following equation [2]:

$$\text{Torsion} = \text{curl } v \cdot z = \frac{\partial v_y}{\partial x} - \frac{\partial v_x}{\partial y} \quad [2]$$

The curl operation yields the rotation of a motion vector v in terms of xyz components. The z-component corresponds to torsion, so the dot product of curl v with the z normal vector is taken whereby the z-component indicates a matrix similarity or a matrix dissimilarity of the radiopaque markers as stent 101*a*/endograft 101*b* is being deployed.

Directionality information may also be determined by torque manager 132 based on a comparison of the radiopaque marker positions within imaged geometrical model(s) to the radiopaque marker positions within the baseline geometrical model as previously described in the present disclosure. More particularly, torsional deployment of stent 101*a*/endograft 101*b* may be detected by torque manager 132 at the following time points of the procedure: (1) after semi-deployment of stent 101*a*/endograft 101*b*, by comparison of the radiopaque marker positions within an intra-operative reconstructed imaged geometrical model to the radiopaque marker positions within a pre-operative reconstructed baseline geometrical model and (2) during continued deployment of stent 101*a*/endograft 101*b*, by comparison of the radiopaque marker positions within a current intra-operative reconstructed imaged geometrical model to the radiopaque marker positions within the pre-operative reconstructed baseline geometrical model, intra-operative reconstructed baseline geometrical model or a hybrid of both.

Motion of the radiopaque markers may optionally be displayed in a number of ways, such as an overlay of miniature arrows, streaking artifact, time lapse, etc. on the vascular medical images 74 (FIG. 9) In case such overlays lead to visual clutter, only alerts on adverse motions may be displayed in such a manner, as separate signage in the visualization, blinking on the overlay, etc.

Intervascular Catheter Imaging.

Figure 11A:
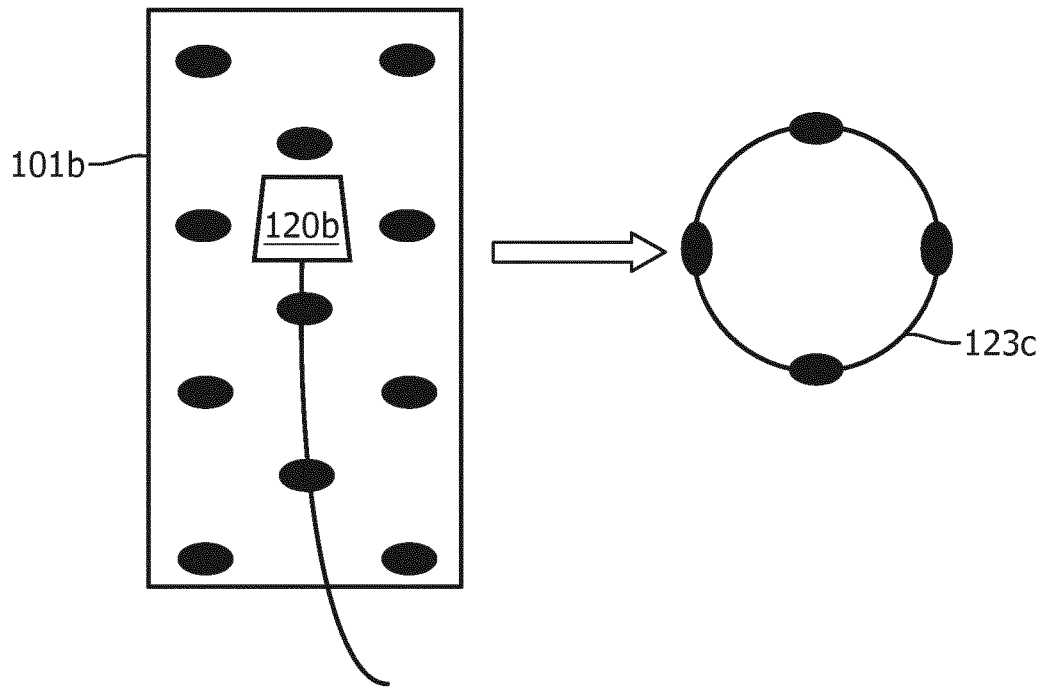
FIGS. 11A and 11B illustrate an exemplary catheter imaging of a vascular therapy device in accordance with the inventive principles of the present disclosure.
Figure 11B:
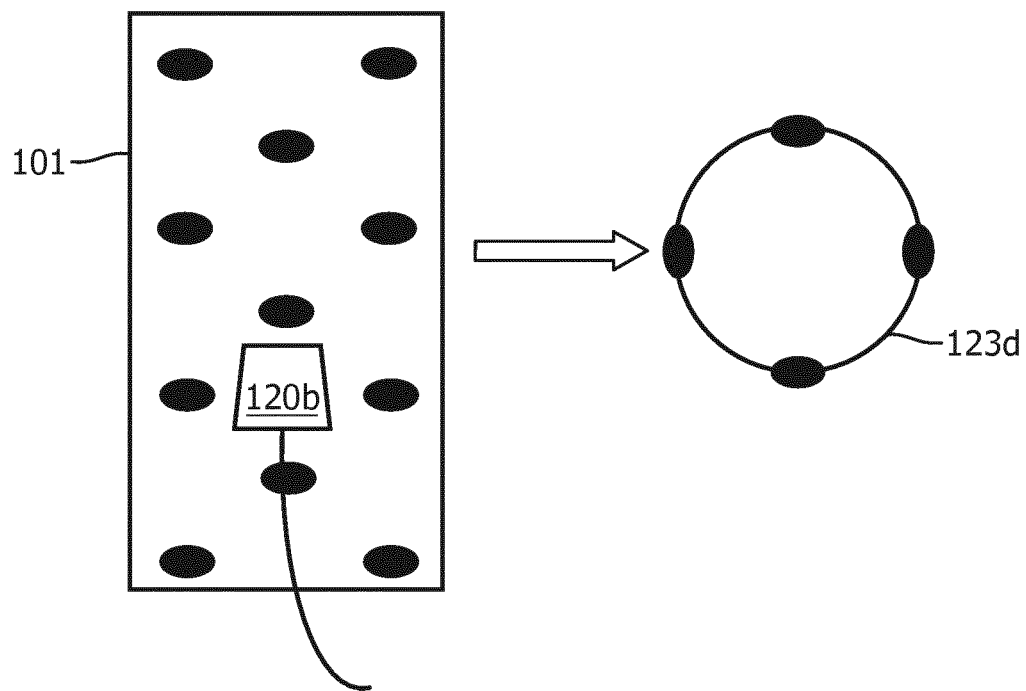

During the endovascular procedure, an intravascular imaging catheter (optical coherence tomography, near infrared imaging, IVUS, etc.) facilitates a monitoring of any torsional buildup within endograft 101*b* as follows:

(1) semi-deploying endograft 101*b* via robot 110 at targeted location within a vascular anatomy as known in the art of the present disclosure;

(2) cannulating endograft 101*b* with an intravascular imaging catheter and perform a pullback to acquire a registration image of the endograft 101*b* (e.g., FIG. 11A and FIG. 11B exemplary illustrate a pullback of intravascular imaging catheter 120*b* to obtain planar images of a rows of imageable markers, such as, rows 123*c* and 123*d* as shown)

(3) an operation of geometry manager 131 to reconstruct an intra-operative baseline geometrical model of endograft 101*b*;

(4) holding the intravascular imaging catheter in place at the level of imageable marker or a row of imageable markers whereby geometry manager 131 reconstructs intra-operative imaged geometrical models of endograft 101*b* around the intravascular imaging catheter, OR additional pullbacks of intravascular imaging catheter could be done to locate multiple markers on the endograft at the level of an additional imageable marker(s) or additional row(s) of imageable markers whereby geometry manager 131 reconstructs intra-operative imaged geometrical models of endograft 101*b* around the intravascular imaging catheter; and (5) an operation of torque manager 131 to compute angular vectors of the imageable markers of endograft 101*b* from the intra-operative imaged geometrical models of endograft 101*b* compared to intra-operative baseline geometrical model of endograft 101*b* as previously described in the present disclosure.

For this imaging to work, it is important for the intravascular imaging catheter to remain fixed in place during an image acquisition or any rotation the intravascular imaging catheter must be monitored via hub as known in the art of the present disclosure.

This intravascular imaging may also be performed for stent 101*a* after removal of balloon 106.

Referring to FIGS. 3-11B, those having ordinary skill in the art of the present disclosure will appreciate numerous benefits of the inventions of the present disclosure including, but not limited to, an automatic detection of a torsional deployment of a vascular therapy device.

Further, as one having ordinary skill in the art will appreciate in view of the teachings provided herein, structures, elements, components, etc. described in the present disclosure/specification and/or depicted in the Figures may be implemented in various combinations of hardware and software, and provide functions which may be combined in a single element or multiple elements. For example, the functions of the various structures, elements, components, etc. shown/illustrated/depicted in the Figures can be provided through the use of dedicated hardware as well as hardware capable of executing software in association with appropriate software for added functionality. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Having described preferred and exemplary embodiments of the various and numerous inventions of the present disclosure (which embodiments are intended to be illustrative and not limiting), it is noted that modifications and variations can be made by persons skilled in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device/system or such as may be used/implemented in/with a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. A torque detection vascular therapy system, comprising:
    a vascular therapy device operable to be transitioned from a pre-deployed state to a post-deployed state,
        wherein the vascular therapy device includes a matrix of imageable markers representative of a geometry of the vascular therapy device; and
    a torque detection controller configured for controlling a detection of one of a non-torsional deployment or a torsional deployment of the vascular therapy device subsequent to a transition of the vascular therapy device from the pre-deployed state to the post-deployed state,
        wherein the torque detection controller is configured to derive compute a motion vector indication of the non-torsional deployment of the vascular therapy device from a matrix orientation similarity between a baseline device geometry of the vascular therapy device represented by the matrix of the imageable markers and an imaged device geometry of the vascular therapy device represented by the matrix of imageable markers, and
        wherein the torque detection controller is configured to compute a motion vector indication of the torsional deployment of the vascular therapy device from a matrix orientation dissimilarity between the baseline device geometry of the vascular therapy device represented by the matrix of the imageable markers and the imaged device geometry of the vascular therapy device represented by the matrix of imageable markers.

2. The torque detection vascular therapy system of claim 1,
wherein the torque detection controller is further configured to at least one of:
reconstruct a pre-deployed geometrical model of the matrix of imageable markers from a device model of the vascular therapy device;
reconstruct the pre-deployed geometrical model of the matrix of imageable markers from at least one extravascular image of the vascular therapy device; and
reconstruct the pre-deployed geometrical model of the matrix of imageable markers from at least one intravascular image of the vascular therapy device; and
wherein the pre-deployed geometrical model of the matrix of imageable markers represents the baseline device geometry of the vascular therapy device.

3. The torque detection vascular therapy system of claim 1,
wherein the torque detection controller is further configured to at least one of:
reconstruct a post-deployed geometrical model of the matrix of imageable markers from at least one extravascular image of the vascular therapy device; and
reconstruct the post-deployed geometrical model of the matrix of imageable markers from at least one intravascular image of the vascular therapy device; and
wherein the post-deployed geometrical model of the matrix of imageable markers represents the imaged device geometry of the vascular therapy device.

4. The torque detection vascular therapy system of claim 1,
wherein the torque detection controller is further configured to compute a motion vector for each imageable marker from the pre-deployed state to the post-deployed state; and
wherein the motion vectors are indicative of one of the matrix orientation similarity or the matrix orientation dissimilarity between the baseline device geometry of the vascular therapy device represented by the matrix of the imageable markers and the imaged device geometry of the vascular therapy device represented by the matrix of the imageable markers.

5. The torque detection vascular therapy system of claim 1,
wherein the torque detection controller is further configured to compute an angular vector of each imageable marker from the pre-deployed state to the post-deployed state; and
wherein the angular vectors are indicative of one of the matrix orientation similarity or the matrix orientation dissimilarity between the baseline device geometry of the vascular therapy device represented by the matrix of the imageable markers and the imaged device geometry of the vascular therapy device represented by the matrix of the imageable markers.

6. The torque detection vascular therapy system of claim 1,
wherein the torque detection controller is further configured to generate an alert informative of a detection of an unacceptable torsional deployment of the vascular therapy device.

7. The torque detection vascular therapy system of claim 1,
wherein the torque detection controller is further configured to control a display of a detection of the torsional deployment of the vascular therapy device.

8. The torque detection vascular therapy system of claim 1, wherein the vascular therapy device further includes an optical shape sensor configured to sense at least one a shape and an orientation of the vascular therapy device.

9. The torque detection vascular therapy system of claim 1, wherein the torque detection controller comprising:
a geometry manager configured to manage a delineation of a baseline device geometry of the vascular therapy device represented by the matrix of the imageable markers subsequent to a transition of the vascular therapy device from a pre-deployed state to a post-deployed state, and a delineation of an imaged device geometry of the vascular therapy device represented by the matrix of imageable markers.

10. The torque detection controller of claim 9,
wherein the geometry manager is further configured to at least one of:
reconstruct a pre-deployed geometrical model of the matrix of imageable markers from a device model of the vascular therapy device;
reconstruct the pre-deployed geometrical model of the matrix of imageable markers from at least one extravascular image of the vascular therapy device; and
reconstruct the pre-deployed geometrical model of the matrix of imageable markers from at least one intravascular image of the vascular therapy device; and
wherein the pre-deployed geometrical model of the matrix of imageable markers represents the baseline device geometry of the vascular therapy device.

11. The torque detection controller of claim 9,
wherein the geometry manager is further configured to at least one of:
reconstruct a post-deployed geometrical model of the matrix of imageable markers from at least one extravascular image of the vascular therapy device; and
reconstruct the post-deployed geometrical model of the matrix of imageable markers from at least one intravascular image of the vascular therapy device; and
wherein the post-deployed geometrical model of the matrix of imageable markers represents the imaged device geometry of the vascular therapy device.

12. The torque detection controller of claim 9,
wherein the torque detector is further configured to compute a motion vector for each imageable marker from the pre-deployed state to the post-deployed state; and
wherein the motion vectors are indicative of one of the matrix orientation similarity or the matrix orientation dissimilarity between the baseline device geometry of the vascular therapy device represented by the matrix of the imageable markers and the imaged device geometry of the vascular therapy device represented by the matrix of the imageable markers.

13. The torque detection controller of claim 9,
wherein the torque detector is further configured to compute an angular vector of each imageable marker from the pre-deployed state to the post-deployed state; and
wherein the angular vectors are indicative of one of the matrix orientation similarity or the matrix orientation dissimilarity between the baseline device geometry of the vascular therapy device represented by the matrix of the imageable markers and the imaged device geometry of the vascular therapy device represented by the matrix of the imageable markers.

14. The torque detection controller of claim 9, wherein the torque detector is further configured to generate an alert informative of detection of an unacceptable torsional deployment of the vascular therapy device.

15. The torque detection controller of claim 9, wherein the torque detector is further configured to control a display of a detection of the torsional deployment of the vascular therapy device.

16. A torque detection method executable by a torque detection controller for detecting one of a non-torsional deployment or a torsional deployment of a vascular therapy device including a matrix imageable markers subsequent to a transition of the vascular therapy device from a pre-deployed state to a post-deployed state, the torque detection method comprising:
the torque detection controller managing a delineation of a baseline device geometry of the vascular therapy device represented by the matrix of the imageable markers and a delineation of a imaged device geometry of the vascular therapy device represented by the matrix of imageable markers; and
one of the torque detection controller deriving the detection of the non-torsional deployment of the vascular therapy device from a matrix orientation similarity between the baseline device geometry of the vascular therapy device represented by the matrix of the imageable markers and the imaged device geometry of the vascular therapy device represented by the matrix of imageable markers or the torque detection controller deriving the detection of the torsional deployment of the vascular therapy device from a matrix orientation dissimilarity between the baseline device geometry of the vascular therapy device represented by the matrix of the imageable markers and the imaged device geometry of the vascular therapy device represented by the matrix of imageable markers.

17. The torque detection method of claim 16, wherein the torque detection controller delineating a baseline device geometry of the vascular therapy device represented by the matrix of the imageable markers and a imaged device geometry of the vascular therapy device represented by the matrix of imageable markers includes at least one of:
the torque detection controller reconstructing a pre-deployed geometrical model of the matrix of imageable markers from a device model of the vascular therapy device;
the torque detection controller reconstructing the pre-deployed geometrical model of the matrix of imageable markers from at least one extravascular image of the vascular therapy device;
the torque detection controller reconstructing the pre-deployed geometrical model of the matrix of imageable markers from at least one intravascular image of the vascular therapy device;
the torque detection controller reconstructing the post-deployed geometrical model of the matrix of imageable markers from at least one extravascular image of the vascular therapy device; and
the torque detection controller reconstructing the post-deployed geometrical model of the matrix of imageable markers from at least one intravascular image of the vascular therapy device;
wherein the pre-deployed geometrical model of the matrix of imageable markers represents the baseline device geometry of the vascular therapy device; and
wherein the post-deployed geometrical model of the matrix of imageable markers represents the imaged device geometry of the vascular therapy device.

18. The torque detection method of claim 16, wherein the torque detection controller deriving the detection of the non-torsional deployment of the vascular therapy device from a matrix orientation similarity between the baseline device geometry of the vascular therapy device represented by the matrix of the imageable markers and the imaged device geometry of the vascular therapy device represented by the matrix of imageable markers includes at least one of:
the torque detection controller computing a motion vector for each imageable marker from the pre-deployed state to the post-deployed state; and
the torque detection controller computing an angular vector of each imageable marker from the pre-deployed state to the post-deployed state;
wherein the motion vectors are indicative of the matrix orientation similarity between the baseline device geometry of the vascular therapy device represented by the matrix of the imageable markers and the imaged device geometry of the vascular therapy device represented by the matrix of the imageable markers; and
wherein the angular vectors are indicative of the matrix orientation similarity between the baseline device geometry of the vascular therapy device represented by the matrix of the imageable markers and the imaged device geometry of the vascular therapy device represented by the matrix of the imageable markers.

19. The torque detection method of claim 16, wherein the torque detection controller deriving the detection of the torsional deployment of the vascular therapy device from the matrix orientation dissimilarity between the baseline device geometry of the vascular therapy device represented by the matrix of the imageable markers and the imaged device geometry of the vascular therapy device represented by the matrix of imageable markers includes at least one of:
the torque detection controller computing a motion vector for each imageable marker from the pre-deployed state to the post-deployed state; and
the torque detection controller computing an angular vector of each imageable marker from the pre-deployed state to the post-deployed state;
wherein the motion vectors are indicative of the matrix orientation dissimilarity between the baseline device geometry of the vascular therapy device represented by the matrix of the imageable markers and the imaged device geometry of the vascular therapy device represented by the matrix of the imageable markers; and
wherein the angular vectors are indicative of the matrix orientation dissimilarity between the baseline device geometry of the vascular therapy device represented by the matrix of the imageable markers and the imaged device geometry of the vascular therapy device represented by the matrix of the imageable markers.

20. The torque detection method of claim 16, further comprising at least one of:
the torque detection controller generating an alert informative of a detection of an unacceptable torsional deployment of the vascular therapy device; and the torque detection controller generating controlling a display of a detection of the torsional deployment of the vascular therapy device.

* * * * *